United States Patent
Bogush et al.

(10) Patent No.: US 9,475,852 B2
(45) Date of Patent: Oct. 25, 2016

(54) METHOD FOR PRODUCING WEB PROTEIN, A FUSED PROTEIN, RECOMBINANT DNA, AN EXPRESSION VECTOR, A HOST CELL AND STRAIN-PRODUCERS

(75) Inventors: Vladimir Grigorievich Bogush, Moscow (RU); Mihail Yurievich Beburov, Moscow (RU); Vladimir Georgievich Debabov, Moscow (RU); Dmitriy Georgievich Kozlov, Moscow (RU); Irek Ilyasovich Gubaydullin, Ufa (RU); Lyubov Ivanovna Davydova, Podolsk (RU); Igor Arsenievich Zalunin, Moscow (RU); Konstantin Vasilievich Sidoruk, Podolsk (RU); Sergey Eduardovich Cheperegin, Lyubertsy (RU)

(73) Assignees: Vladimir Grigorievich Bogush, Moscow (RU); Mihail Yurievich Beburov, Moscow (RU); Vladimir Georgievich Debabov, Moscow (RU)

(*) Notice: Subject to any disclaimer, the term of this patent is extended or adjusted under 35 U.S.C. 154(b) by 67 days.

(21) Appl. No.: 13/989,727

(22) PCT Filed: Dec. 13, 2010

(86) PCT No.: PCT/RU2010/000752
§ 371 (c)(1),
(2), (4) Date: Aug. 12, 2013

(87) PCT Pub. No.: WO2012/070977
PCT Pub. Date: May 31, 2012

(65) Prior Publication Data
US 2014/0094589 A1    Apr. 3, 2014

(30) Foreign Application Priority Data
Nov. 25, 2010    (RU) .................. 2010148011

(51) Int. Cl.
C07K 14/435    (2006.01)
C12N 15/81    (2006.01)
C12R 1/865    (2006.01)

(52) U.S. Cl.
CPC ......... *C07K 14/43518* (2013.01); *C12N 15/81* (2013.01); *C12R 1/865* (2013.01); *C07K 2319/95* (2013.01)

(58) Field of Classification Search
None
See application file for complete search history.

(56) References Cited

U.S. PATENT DOCUMENTS

| 5,728,810 A | 3/1998 | Lewis et al. |
| 6,068,994 A | 5/2000 | Barr |
| 7,521,228 B2* | 4/2009 | Lewis et al. ............... 435/320.1 |

FOREIGN PATENT DOCUMENTS

| WO | 2006008163 A2 | 1/2006 |
| WO | 2008083271 A2 | 7/2008 |

OTHER PUBLICATIONS

Marblestone et al., Comparison of SUMO fusion technology with traditional gene fusion systems: Enhanced expression and solubility with SUMO, Protein Science (2006), vol. 15, pp. 182-189.*
(Continued)

*Primary Examiner* — Alexander Kim
(74) *Attorney, Agent, or Firm* — Porzio, Bromberg & Newman, P.C.

(57) ABSTRACT

The invention relates to the field of biotechnology and provides a method for producing recombinant proteins from the orb-weaving spider silk in yeast cells. This involves the construction of an expression vector which comprises a DNA sequence encoding a recombinant protein of the orb-weaving spider silk fused with a sequence encoding an ubiquitin-like protein occupying an N-terminal position with respect to the spider silk recombinant protein within the fused protein. The expression of a hybrid gene makes it possible to increase tens of times the production of recombinant spider silk protein, wherein the recombinant protein accumulates in the yeast cells in a water-insoluble fraction in the form of a processed protein free of a hybrid component.

The invention also relates to fused proteins comprising sequences of recombinant proteins of the orb-weaving spider silk and of ubiquitin-like proteins, to recombinant DNAs encoding the fused proteins, to host yeast cells and to expression vectors suitable for carrying out the method, and also to producer strains of recombinant proteins of the orb-weaving spider silk.

3 Claims, 5 Drawing Sheets

(56) References Cited

OTHER PUBLICATIONS

Muller et al., "SUMO, Ubiquitin's Mysterious Cousin", Nature Reviews: Molecular Cellular Biology, vol. 2 (Mar. 2001), 202-210.
Mossessova et al., "Ulp1-SUMO Crystal Structure and Genetic Analysis Reveal Conserved Interactions and a Regulatory Element Essential for Cell Growth in Yeast", Molecular Cell., vol. 5 (May 2000), 865-876.
Hu et al., "Molecular Mechanisms of Spider Silk", Cell. Mol. Life Sci., vol. 63 (2006), 1986-1999.
Guerette et al., "Silk Properties Determined by Gland-Specific Expression of a Spider Fibroin Gene Family", Science, vol. 272 (Apr. 5, 1996), 112-115.
Winkler et al., "Designing Recombinant Spider Silk Proteins to Controls Assembly", Int. J. of Biological Macromolecules, vol. 24 (1999), 265-270.
Hayashi et al., "Hypotheses that Correlate the Sequence, Structure, and Mechanical Properties of Spider Silk Proteins", Int. J. of Biological Macromolecules, vol. 24 (1999), 271-275.
Shatzman et al., "Expression, Identification, and Characterization of Recombinant Gene Products in *Escherichia coli*", Methods in Enzymology, vol. 152 (1987), 661-673.
Xu et al., "Structure of a Protein Superfiber: Spider Dragline Silk", Proc. Natl. Acad. SCi. USA, vol. 87 (Sep. 1990), 7120-7124.
Colgin et al., "Spider Minor Ampullate Silk Proteins Contain New Repetitive Sequences and Highly Conserved Non-Silk-Like 'Spacer Regions'", Protein Science, vol. 7 (1998), 667-672.
Kohler et al., "Thread Biomechanics in the Two Orb-Weaving Spiders *Araneus diadematus* (*Araneae, Araneidae*) and *Uloborus walckenaerius* (*Araneae, Uloboridae*)", J. of Experimental Zoology, vol. 271 (1995), 1-17.
Prince et al., "Construction, Cloning, and Expression of Synthetic Genes Encoding Spider Dragline Silk", Biochemistry, vol. 34 (1995), 10879-10885.
Gosline et al., "The Structure and Properties of Spider Silk", Endeavour, vol. 10: No. 1 (1986), 37-43.
Arcidiacono et al., "Purification and Characterization of Recombinant Spider Silk Expressed in *Escherichia coli*", Appl. Microbiol. Biotechnol., vol. 49 (1998), 31-38.
Bogush et al., "Obtaining, Purification, and Silking of Recombinant Analog of Spidroin 1", 2006.
Hinman et al., "Synthetic Spider Silk: A Modular Fiber", Tibtech, vol. 18 (Sep. 2000), 374-379.
Muller et al., "Conjugation with the Ubiquitin-Related Modifier SUMO-1 Regulates the Partitioning of PML Within the Nucleus", The EMBO Journal, vol. 17: No. 1 (1998), 61-70.
Johnson et al., "The Ubiquitin-Like Protein Smt3p is Activated for Conjugation to Other Proteins by an Aos1p/Uba2p Heterodimer", The EMBO Journal, vol. 16: No. 18 (1997), 5509-5519.
Hayashi et al., "Evidence from Flagelliform Silk cDNA for the Structural Basis of Elasticity and Modular Nature of Spider Silks", J. Mol. Biol., vol. 275 (1998), 773-784.
Scheller et al., "Purification of Spider Silk-Elastin from Transgenic Plants and Application for Human Chondrocyte Proliferation", Transfenic Research, vol. 13 (2004), 51-57.
Lewis et al., "Expression and Purification of a Spider Silk Protein: A New Strategy for Producing Repetitive Proteins", Protein Expression and Purification, vol. 7 (1996), 400-406.
Malakhov et al., "SUMO Fusions and SUMO-Specific Protease for Efficient Expression and Purification of Proteins", J. of Structural and Functional Genomics, vol. 5 (2004), 75-86.
Fahnestock et al., "Production of Synthetic Spider Dragline Silk Protein in Pichia Pastoris", Appl. Microbiol. Biotechnol., vol. 47 (1997), 33-39.
Huemmerich et al., "Primary Structure Elements of Spider Dragline Silks and Their Contribution to Protein Solubility", Biochemistry, vol. 43 (2004), 13604-13612.
Bogush et al., "A Novel Model System for Design of Biomaterials Based on Recombinant Analogs of Spider Silk Proteins", J. Neuroimmune. Pharmacol., (Mar. 2008), DOI 10.1007/s11481-008-9129-z.
Hinman et al., "Isolation of a Clone Encoding a Second Dragline Silk Fibroin", J. of Biol. Chem., vol. 267: No. 27 (Sep. 25, 1992), 19320-19324.
Fahnestock et al., "Synthetic Spider Dragline Silk Proteins and Their Production in *Escherichia Coli*", Appl. Microbiol. Biotechnol., vol. 47 (1997), 23-32.
Butt et al., "SUMO Fusion Technology for Difficult-To-Express Proteins", Protein Expression and Purification, (2005).

\* cited by examiner

SEQUENCE LISTING

```
<160> NUMBER OF SEQ ID NOS: 34

<210> SEQ ID NO 1
<211> LENGTH: 1302
<212> TYPE: PRT
<213> ORGANISM: Artificial Sequence
<220> FEATURE:
<223> OTHER INFORMATION: Description of Artificial Sequence: Synthetic
      amino acid sequence of fusion protein HUB-1F9 consisting of a
      synthetic sequence of a hexa-histidine tag, protein ubiquitin
      sequence from Saccharomyces cerevisiae and synthetic protein 1F9

<400> SEQUENCE: 1

Met Glu His His His His His His Gly Gly Met Gln Ile Phe Val Lys
1               5                   10                  15

Thr Leu Thr Gly Lys Thr Ile Thr Leu Glu Val Glu Ser Ser Asp Thr
                20                  25                  30

Ile Asp Asn Val Lys Ser Lys Ile Gln Asp Lys Glu Gly Ile Pro Pro
            35                  40                  45

Asp Gln Gln Arg Leu Ile Phe Ala Gly Lys Gln Leu Glu Asp Gly Arg
        50                  55                  60

Thr Leu Ser Asp Tyr Asn Ile Gln Lys Glu Ser Thr Leu His Leu Val
65                  70                  75                  80

Leu Arg Leu Arg Gly Gly Ser Gln Gly Ala Gly Gln Gly Gly Tyr Gly
                85                  90                  95

Gly Leu Gly Ser Gln Gly Ala Gly Arg Gly Gly Leu Gly Gly Gln Gly
                100                 105                 110

Ala Gly Ala Ala Ala Ala Ala Ala Gly Gly Ala Gly Gln Gly Gly
            115                 120                 125

Leu Gly Gly Gln Gly Ala Gly Gln Gly Ala Gly Ala Ala Ala Ala
        130                 135                 140

Ala Gly Gly Ala Gly Gln Gly Gly Tyr Gly Gly Leu Gly Ser Gln Gly
145                 150                 155                 160

Ala Gly Arg Gly Gly Leu Gly Gly Gln Gly Ala Gly Ala Ala Ala Ala
                165                 170                 175

Ala Ala Ala Gly Gly Ala Gly Gln Gly Gly Tyr Gly Gly Leu Gly Ser
                180                 185                 190

Gln Gly Ala Gly Arg Gly Gly Gln Gly Ala Gly Ala Ala Ala Ala
            195                 200                 205

Ala Gly Gly Ala Gly Gln Gly Gly Tyr Gly Gly Leu Gly Ser Gln Gly
        210                 215                 220

Ala Gly Gln Gly Gly Tyr Gly Gly Leu Gly Ser Gln Gly Ala Gly Arg
225                 230                 235                 240

Gly Gly Leu Gly Gly Gln Gly Ala Gly Ala Ala Ala Ala Ala Ala Ala
                245                 250                 255

Gly Gly Ala Gly Gln Gly Gly Leu Gly Gly Gln Gly Ala Gly Gln Gly
            260                 265                 270
```

```
Ala Gly Ala Ala Ala Ala Ala Gly Gly Ala Gly Gln Gly Gly Tyr
            275                 280                 285
Gly Gly Leu Gly Ser Gln Gly Ala Gly Arg Gly Gly Leu Gly Gly Gln
        290                 295                 300
Gly Ala Gly Ala Ala Ala Ala Ala Ala Gly Gly Ala Gly Gln Gly
305                 310                 315                 320
Gly Tyr Gly Gly Leu Gly Ser Gln Gly Ala Gly Arg Gly Gly Gln Gly
                325                 330                 335
Ala Gly Ala Ala Ala Ala Ala Gly Ala Gly Gln Gly Gly Tyr
            340                 345                 350
Gly Gly Leu Gly Ser Gln Gly Ala Gly Gln Gly Gly Tyr Gly Gly Leu
        355                 360                 365
Gly Ser Gln Gly Ala Gly Arg Gly Gly Leu Gly Gly Gln Gly Ala Gly
        370                 375                 380
Ala Ala Ala Ala Ala Ala Gly Gly Ala Gly Gln Gly Gly Leu Gly
385                 390                 395                 400
Gly Gln Gly Ala Gly Gln Gly Ala Gly Ala Ala Ala Ala Ala Gly
            405                 410                 415
Gly Ala Gly Gln Gly Gly Tyr Gly Gly Leu Gly Ser Gln Gly Ala Gly
            420                 425                 430
Arg Gly Gly Leu Gly Gly Gln Gly Ala Gly Ala Ala Ala Ala Ala
        435                 440                 445
Ala Gly Ala Gly Gln Gly Gly Tyr Gly Gly Leu Gly Ser Gln Gly
        450                 455                 460
Ala Gly Arg Gly Gly Gln Gly Ala Gly Ala Ala Ala Ala Ala Gly
465                 470                 475                 480
Gly Ala Gly Gln Gly Gly Tyr Gly Gly Leu Gly Ser Gln Gly Ala Gly
            485                 490                 495
Gln Gly Gly Tyr Gly Gly Leu Gly Ser Gln Gly Ala Gly Arg Gly Gly
                500                 505                 510
Leu Gly Gly Gln Gly Ala Gly Ala Ala Ala Ala Ala Ala Gly Gly
        515                 520                 525
Ala Gly Gln Gly Gly Leu Gly Gly Gln Gly Ala Gly Gln Gly Ala Gly
        530                 535                 540
Ala Ala Ala Ala Ala Ala Gly Gly Ala Gly Gln Gly Gly Tyr Gly Gly
545                 550                 555                 560
Leu Gly Ser Gln Gly Ala Gly Arg Gly Gly Leu Gly Gly Gln Gly Ala
                565                 570                 575
Gly Ala Ala Ala Ala Ala Ala Gly Gly Ala Gly Gln Gly Gly Tyr
            580                 585                 590
Gly Gly Leu Gly Ser Gln Gly Ala Gly Arg Gly Gly Gln Gly Ala Gly
        595                 600                 605
Ala Ala Ala Ala Ala Gly Gly Ala Gly Gln Gly Gly Tyr Gly Gly
610                 615                 620
Leu Gly Ser Gln Gly Ala Gly Gln Gly Gly Tyr Gly Gly Leu Gly Ser
625                 630                 635                 640
Gln Gly Ala Gly Arg Gly Gly Leu Gly Gly Gln Gly Ala Gly Ala Ala
                645                 650                 655
Ala Ala Ala Ala Ala Gly Gly Ala Gly Gln Gly Gly Leu Gly Gln
            660                 665                 670
Gly Ala Gly Gln Gly Ala Gly Ala Ala Ala Ala Ala Ala Gly Gly Ala
        675                 680                 685
Gly Gln Gly Gly Tyr Gly Gly Leu Gly Ser Gln Gly Ala Gly Arg Gly
```

```
                690                  695                 700
Gly Leu Gly Gly Gln Gly Ala Gly Ala Ala Ala Ala Ala Ala Gly
705                 710                 715                 720

Gly Ala Gly Gln Gly Gly Tyr Gly Gly Leu Gly Ser Gln Gly Ala Gly
                725                 730                 735

Arg Gly Gly Gln Gly Ala Gly Ala Ala Ala Ala Ala Gly Gly Ala
                740                 745                 750

Gly Gln Gly Gly Tyr Gly Gly Leu Gly Ser Gln Gly Ala Gly Gln Gly
                755                 760                 765

Gly Tyr Gly Gly Leu Gly Ser Gln Gly Ala Gly Arg Gly Gly Leu Gly
                770                 775                 780

Gly Gln Gly Ala Gly Ala Ala Ala Ala Ala Ala Gly Gly Ala Gly
785                 790                 795                 800

Gln Gly Gly Leu Gly Gly Gln Gly Ala Gly Gln Gly Ala Gly Ala Ala
                805                 810                 815

Ala Ala Ala Ala Gly Gly Ala Gly Gln Gly Gly Tyr Gly Gly Leu Gly
                820                 825                 830

Ser Gln Gly Ala Gly Arg Gly Gly Leu Gly Gly Gln Gly Ala Gly Ala
                835                 840                 845

Ala Ala Ala Ala Ala Gly Gly Ala Gly Gln Gly Gly Tyr Gly Gly
850                 855                 860

Leu Gly Ser Gln Gly Ala Gly Arg Gly Gly Gln Gly Ala Gly Ala Ala
865                 870                 875                 880

Ala Ala Ala Ala Gly Gly Ala Gly Gln Gly Gly Tyr Gly Gly Leu Gly
                885                 890                 895

Ser Gln Gly Ala Gly Gln Gly Gly Tyr Gly Gly Leu Gly Ser Gln Gly
                900                 905                 910

Ala Gly Arg Gly Gly Leu Gly Gly Gln Gly Ala Gly Ala Ala Ala Ala
                915                 920                 925

Ala Ala Ala Gly Gly Ala Gly Gln Gly Gly Leu Gly Gly Gln Gly Ala
                930                 935                 940

Gly Gln Gly Ala Gly Ala Ala Ala Ala Ala Gly Gly Ala Gly Gln
945                 950                 955                 960

Gly Gly Tyr Gly Gly Leu Gly Ser Gln Gly Ala Gly Arg Gly Gly Leu
                965                 970                 975

Gly Gly Gln Gly Ala Gly Ala Ala Ala Ala Ala Ala Gly Gly Ala
                980                 985                 990

Gly Gln Gly Gly Tyr Gly Gly Leu Gly Ser Gln Gly Ala Gly Arg Gly
                995                 1000                1005

Gly Gln Gly Ala Gly Ala Ala Ala Ala Ala Ala Gly Gly Ala Gly
1010                1015                1020

Gln Gly Gly Tyr Gly Gly Leu Gly Ser Gln Gly Ala Gly Gln Gly
                1025                1030                1035

Gly Tyr Gly Gly Leu Gly Ser Gln Gly Ala Gly Arg Gly Gly Leu
                1040                1045                1050

Gly Gly Gln Gly Ala Gly Ala Ala Ala Ala Ala Ala Gly Gly
                1055                1060                1065

Ala Gly Gln Gly Gly Leu Gly Gly Gln Gly Ala Gly Gln Gly Ala
                1070                1075                1080

Gly Ala Ala Ala Ala Ala Ala Gly Gly Ala Gly Gln Gly Gly Tyr
                1085                1090                1095

Gly Gly Leu Gly Ser Gln Gly Ala Gly Arg Gly Gly Leu Gly Gly
                1100                1105                1110
```

-continued

Gln Gly Ala Gly Ala Ala Ala Ala Ala Ala Gly Gly Ala Gly
    1115                1120                1125

Gln Gly Gly Tyr Gly Gly Leu Gly Ser Gln Gly Ala Gly Arg Gly
    1130                1135                1140

Gly Gln Gly Ala Gly Ala Ala Ala Ala Ala Ala Gly Gly Ala Gly
    1145                1150                1155

Gln Gly Gly Tyr Gly Gly Leu Gly Ser Gln Gly Ala Gly Gln Gly
    1160                1165                1170

Gly Tyr Gly Gly Leu Gly Ser Gln Gly Ala Gly Arg Gly Gly Leu
    1175                1180                1185

Gly Gly Gln Gly Ala Gly Ala Ala Ala Ala Ala Ala Gly Gly
    1190                1195                1200

Ala Gly Gln Gly Gly Leu Gly Gly Gln Gly Ala Gly Gln Gly Ala
    1205                1210                1215

Gly Ala Ala Ala Ala Ala Gly Gly Ala Gly Gln Gly Gly Tyr
    1220                1225                1230

Gly Gly Leu Gly Ser Gln Gly Ala Gly Arg Gly Gly Leu Gly Gly
    1235                1240                1245

Gln Gly Ala Gly Ala Ala Ala Ala Ala Ala Gly Gly Ala Gly
    1250                1255                1260

Gln Gly Gly Tyr Gly Gly Leu Gly Ser Gln Gly Ala Gly Arg Gly
    1265                1270                1275

Gly Gln Gly Ala Gly Ala Ala Ala Ala Ala Ala Gly Gly Ala Gly
    1280                1285                1290

Gln Arg Gly Tyr Gly Gly Leu Gly Ser
    1295                1300

<210> SEQ ID NO 2
<211> LENGTH: 1494
<212> TYPE: PRT
<213> ORGANISM: Artificial Sequence
<220> FEATURE:
<223> OTHER INFORMATION: Description of Artificial Sequence: Synthetic
      amino acid sequence of fusion protein HUB-2E12 consisting of a
      synthetic sequence of a hexa-histidine tag, protein ubiquitin
      sequence from Saccharomyces cerevisiae and synthetic protein 2E12

<400> SEQUENCE: 2

Met Glu His His His His His Gly Gly Met Gln Ile Phe Val Lys
1               5                   10                  15

Thr Leu Thr Gly Lys Thr Ile Thr Leu Glu Val Glu Ser Ser Asp Thr
            20                  25                  30

Ile Asp Asn Val Lys Ser Lys Ile Gln Asp Lys Glu Gly Ile Pro Pro
        35                  40                  45

Asp Gln Gln Arg Leu Ile Phe Ala Gly Lys Gln Leu Glu Asp Gly Arg
    50                  55                  60

Thr Leu Ser Asp Tyr Asn Ile Gln Lys Glu Ser Thr Leu His Leu Val
65                  70                  75                  80

Leu Arg Leu Arg Gly Gly Ser Gly Pro Gly Gly Tyr Gly Pro Gly Gln
                85                  90                  95

Gln Gly Pro Gly Ala Ala Ala Ala Ser Ala Gly Arg Gly Pro Gly
            100                 105                 110

Gly Tyr Gly Pro Gly Gln Gln Gly Pro Gly Gly Ser Gly Ala Ala Ala
        115                 120                 125

Ala Ala Ala Gly Ser Gly Pro Gly Gly Tyr Gly Pro Gly Gln Gln Gly
    130                 135                 140

```
Pro Gly Gly Pro Gly Ala Ala Ala Ala Ala Gly Arg Gly Pro
145                 150                 155             160

Gly Gly Tyr Gly Pro Gly Gln Gln Gly Pro Gly Ser Gly Ala Ala
            165                 170                 175

Ala Ala Ala Ala Gly Arg Gly Pro Gly Gly Tyr Gly Pro Gly Gln Gln
        180                 185                 190

Gly Pro Gly Pro Gly Ala Ala Ala Ala Gly Pro Gly Gly
        195                 200                 205

Tyr Gly Pro Gly Gln Gln Gly Pro Gly Ala Ala Ala Ala Ser Ala
        210                 215                 220

Gly Arg Gly Pro Gly Gly Tyr Gly Pro Gly Gln Gln Gly Pro Gly Gly
225                 230                 235                 240

Ser Gly Ala Ala Ala Ala Ala Gly Ser Gly Pro Gly Gly Tyr Gly
            245                 250                 255

Pro Gly Gln Gln Gly Pro Gly Pro Gly Ala Ala Ala Ala Ala
            260                 265                 270

Ala Gly Arg Gly Pro Gly Gly Tyr Gly Pro Gly Gln Gln Gly Pro Gly
        275                 280                 285

Gly Ser Gly Ala Ala Ala Ala Ala Gly Arg Gly Pro Gly Gly Tyr
    290                 295                 300

Gly Pro Gly Gln Gln Gly Pro Gly Pro Gly Ala Ala Ala Ala
305                 310                 315                 320

Ala Gly Pro Gly Gly Tyr Gly Pro Gly Gln Gln Gly Pro Gly Ala Ala
            325                 330                 335

Ala Ala Ala Ser Ala Gly Arg Gly Pro Gly Gly Tyr Gly Pro Gly Gln
            340                 345                 350

Gln Gly Pro Gly Gly Ser Gly Ala Ala Ala Ala Gly Ser Gly
            355                 360                 365

Pro Gly Gly Tyr Gly Pro Gly Gln Gln Gly Pro Gly Gly Pro Gly Ala
        370                 375                 380

Ala Ala Ala Ala Ala Gly Arg Gly Pro Gly Gly Tyr Gly Pro Gly
385                 390                 395                 400

Gln Gln Gly Pro Gly Gly Ser Gly Ala Ala Ala Ala Ala Gly Arg
            405                 410                 415

Gly Pro Gly Gly Tyr Gly Pro Gly Gln Gln Gly Pro Gly Gly Pro Gly
            420                 425                 430

Ala Ala Ala Ala Ala Gly Pro Gly Gly Tyr Gly Pro Gly Gln Gln
        435                 440                 445

Gly Pro Gly Ala Ala Ala Ala Ser Ala Gly Arg Gly Pro Gly Gly
    450                 455                 460

Tyr Gly Pro Gly Gln Gln Gly Pro Gly Gly Ser Gly Ala Ala Ala Ala
465                 470                 475                 480

Ala Ala Gly Ser Gly Pro Gly Gly Tyr Gly Pro Gly Gln Gln Gly Pro
        485                 490                 495

Gly Gly Pro Gly Ala Ala Ala Ala Ala Ala Gly Arg Gly Pro Gly
        500                 505                 510

Gly Tyr Gly Pro Gly Gln Gln Gly Pro Gly Ser Gly Ala Ala Ala
    515                 520                 525

Ala Ala Ala Gly Arg Gly Pro Gly Gly Tyr Gly Pro Gly Gln Gln Gly
        530                 535                 540

Pro Gly Gly Pro Gly Ala Ala Ala Ala Ala Gly Pro Gly Gly Tyr
545                 550                 555                 560
```

-continued

```
Gly Pro Gly Gln Gln Gly Pro Gly Ala Ala Ala Ala Ser Ala Gly
            565                 570                 575

Arg Gly Pro Gly Gly Tyr Gly Pro Gly Gln Gln Gly Pro Gly Gly Ser
            580                 585                 590

Gly Ala Ala Ala Ala Ala Gly Ser Gly Pro Gly Gly Tyr Gly Pro
            595                 600                 605

Gly Gln Gln Gly Pro Gly Pro Gly Ala Ala Ala Ala Ala
            610                 615                 620

Gly Arg Gly Pro Gly Gly Tyr Gly Pro Gly Gln Gln Gly Pro Gly Gly
625                 630                 635                 640

Ser Gly Ala Ala Ala Ala Ala Gly Arg Gly Pro Gly Gly Tyr Gly
            645                 650                 655

Pro Gly Gln Gln Gly Pro Gly Gly Pro Gly Ala Ala Ala Ala Ala
            660                 665                 670

Gly Pro Gly Gly Tyr Gly Pro Gly Gln Gln Gly Pro Gly Ala Ala Ala
            675                 680                 685

Ala Ala Ser Ala Gly Arg Gly Pro Gly Gly Tyr Gly Pro Gly Gln Gln
            690                 695                 700

Gly Pro Gly Gly Ser Gly Ala Ala Ala Ala Ala Gly Ser Gly Pro
705                 710                 715                 720

Gly Gly Tyr Gly Pro Gly Gln Gln Gly Pro Gly Pro Gly Ala Ala
            725                 730                 735

Ala Ala Ala Ala Gly Arg Gly Pro Gly Gly Tyr Gly Pro Gly Gln
            740                 745                 750

Gln Gly Pro Gly Gly Ser Gly Ala Ala Ala Ala Ala Gly Arg Gly
            755                 760                 765

Pro Gly Gly Tyr Gly Pro Gly Gln Gln Gly Pro Gly Gly Pro Gly Ala
            770                 775                 780

Ala Ala Ala Ala Gly Pro Gly Gly Tyr Gly Pro Gly Gln Gln Gly
785                 790                 795                 800

Pro Gly Ala Ala Ala Ala Ser Ala Gly Arg Gly Pro Gly Gly Tyr
            805                 810                 815

Gly Pro Gly Gln Gln Gly Pro Gly Gly Ser Gly Ala Ala Ala Ala
            820                 825                 830

Ala Gly Ser Gly Pro Gly Gly Tyr Gly Pro Gly Gln Gln Gly Pro Gly
            835                 840                 845

Gly Pro Gly Ala Ala Ala Ala Ala Ala Gly Arg Gly Pro Gly Gly
            850                 855                 860

Tyr Gly Pro Gly Gln Gln Gly Pro Gly Gly Ser Gly Ala Ala Ala Ala
865                 870                 875                 880

Ala Ala Gly Arg Gly Pro Gly Gly Tyr Gly Pro Gly Gln Gln Gly Pro
            885                 890                 895

Gly Gly Pro Gly Ala Ala Ala Ala Ala Gly Pro Gly Gly Tyr Gly
            900                 905                 910

Pro Gly Gln Gln Gly Pro Gly Ala Ala Ala Ala Ser Ala Gly Arg
            915                 920                 925

Gly Pro Gly Gly Tyr Gly Pro Gly Gln Gln Gly Pro Gly Gly Ser Gly
            930                 935                 940

Ala Ala Ala Ala Ala Gly Ser Gly Pro Gly Gly Tyr Gly Pro Gly
945                 950                 955                 960

Gln Gln Gly Pro Gly Pro Gly Ala Ala Ala Ala Ala Ala Gly
            965                 970                 975

Arg Gly Pro Gly Gly Tyr Gly Pro Gly Gln Gln Gly Pro Gly Gly Ser
```

-continued

```
            980             985             990
Gly Ala Ala Ala Ala Ala Ala Gly Arg Gly Pro Gly Gly Tyr Gly Pro
                995            1000               1005
Gly Gln Gln Gly Pro Gly Gly Pro Gly Ala Ala Ala Ala Ala Ala
       1010             1015                1020
Gly Pro Gly Gly Tyr Gly Pro Gly Gln Gln Gly Pro Gly Ala Ala
       1025             1030                1035
Ala Ala Ala Ser Ala Gly Arg Gly Pro Gly Gly Tyr Gly Pro Gly
       1040             1045                1050
Gln Gln Gly Pro Gly Gly Ser Gly Ala Ala Ala Ala Ala Ala Gly
       1055             1060                1065
Ser Gly Pro Gly Gly Tyr Gly Pro Gly Gln Gln Gly Pro Gly Gly
       1070             1075                1080
Pro Gly Ala Ala Ala Ala Ala Ala Ala Gly Arg Gly Pro Gly Gly
       1085             1090                1095
Tyr Gly Pro Gly Gln Gln Gly Pro Gly Gly Ser Gly Ala Ala Ala
       1100             1105                1110
Ala Ala Ala Gly Arg Gly Pro Gly Gly Tyr Gly Pro Gly Gln Gln
       1115             1120                1125
Gly Pro Gly Gly Pro Gly Ala Ala Ala Ala Ala Ala Gly Pro Gly
       1130             1135                1140
Gly Tyr Gly Pro Gly Gln Gln Gly Pro Gly Ala Ala Ala Ala Ala
       1145             1150                1155
Ser Ala Gly Arg Gly Pro Gly Gly Tyr Gly Pro Gly Gln Gln Gly
       1160             1165                1170
Pro Gly Gly Ser Gly Ala Ala Ala Ala Ala Ala Gly Ser Gly Pro
       1175             1180                1185
Gly Gly Tyr Gly Pro Gly Gln Gln Gly Pro Gly Gly Pro Gly Ala
       1190             1195                1200
Ala Ala Ala Ala Ala Gly Arg Gly Pro Gly Gly Tyr Gly Pro
       1205             1210                1215
Gly Gln Gln Gly Pro Gly Gly Ser Gly Ala Ala Ala Ala Ala Ala
       1220             1225                1230
Gly Arg Gly Pro Gly Gly Tyr Gly Pro Gly Gln Gln Gly Pro Gly
       1235             1240                1245
Gly Pro Gly Ala Ala Ala Ala Ala Ala Gly Pro Gly Gly Tyr Gly
       1250             1255                1260
Pro Gly Gln Gln Gly Pro Gly Ala Ala Ala Ala Ala Ser Ala Gly
       1265             1270                1275
Arg Gly Pro Gly Gly Tyr Gly Pro Gly Gln Gln Gly Pro Gly Gly
       1280             1285                1290
Ser Gly Ala Ala Ala Ala Ala Ala Gly Ser Gly Pro Gly Gly Tyr
       1295             1300                1305
Gly Pro Gly Gln Gln Gly Pro Gly Gly Pro Gly Ala Ala Ala Ala
       1310             1315                1320
Ala Ala Ala Gly Arg Gly Pro Gly Gly Tyr Gly Pro Gly Gln Gln
       1325             1330                1335
Gly Pro Gly Gly Ser Gly Ala Ala Ala Ala Ala Gly Arg Gly
       1340             1345                1350
Pro Gly Gly Tyr Gly Pro Gly Gln Gln Gly Pro Gly Gly Pro Gly
       1355             1360                1365
Ala Ala Ala Ala Ala Ala Gly Pro Gly Gly Tyr Gly Pro Gly Gln
       1370             1375                1380
```

```
Gln Gly Pro Gly Ala Ala  Ala Ala Ser Ala Gly  Arg Gly Pro
    1385              1390              1395

Gly Gly Tyr Gly Pro Gly  Gln Gln Gly Pro Gly  Gly Ser Gly Ala
    1400              1405              1410

Ala Ala Ala Ala Ala Gly  Ser Gly Pro Gly Gly  Tyr Gly Pro Gly
    1415              1420              1425

Gln Gln Gly Pro Gly Gly  Pro Gly Ala Ala Ala  Ala Ala Ala
    1430              1435              1440

Gly Arg Gly Pro Gly Gly  Tyr Gly Pro Gly Gln  Gln Gly Pro Gly
    1445              1450              1455

Gly Ser Gly Ala Ala Ala  Ala Ala Gly Arg Gly  Pro Gly Gly
    1460              1465              1470

Tyr Gly Pro Gly Gln Gln Gly  Pro Gly Gly Pro Gly  Ala Ala Ala
    1475              1480              1485

Ala Ala Ala Gly Gly Ser
    1490
```

<210> SEQ ID NO 3
<211> LENGTH: 1316
<212> TYPE: PRT
<213> ORGANISM: Artificial Sequence
<220> FEATURE:
<223> OTHER INFORMATION: Description of Artificial Sequence: Synthetic
      amino acid sequence of fusion protein SUMO-1F9 consisting of SMT3
      protein sequence from Saccharomyces cerevisiae and synthetic
      protein 1F9

<400> SEQUENCE: 3

```
Met His Gly Ser Asp Ser  Glu Val Asn Gln Glu  Ala Lys Pro Glu Val
1               5                   10                  15

Lys Pro Glu Val Lys Pro  Glu Thr His Ile Asn  Leu Lys Val Ser Asp
                20                  25                  30

Gly Ser Ser Glu Ile Phe  Phe Lys Ile Lys Lys  Thr Thr Pro Leu Arg
            35                  40                  45

Arg Leu Met Glu Ala Phe  Ala Lys Arg Gln Gly  Lys Glu Met Asp Ser
50                  55                  60

Leu Arg Phe Leu Tyr Asp  Gly Ile Arg Ile Gln  Ala Asp Gln Thr Pro
65                  70                  75                  80

Glu Asp Leu Asp Met Glu  Asp Asn Asp Ile Ile  Glu Ala His Arg Glu
                85                  90                  95

Gln Ile Gly Gly Ser Gln  Gly Ala Gly Gln Gly  Gly Tyr Gly Gly Leu
            100                 105                 110

Gly Ser Gln Gly Ala Gly  Arg Gly Gly Leu Gly  Gly Gln Gly Ala Gly
        115                 120                 125

Ala Ala Ala Ala Ala Ala  Gly Gly Ala Gly Gln  Gly Gly Leu Gly
    130                 135                 140

Gly Gln Gly Ala Gly Gln  Gly Ala Gly Ala Ala  Ala Ala Ala Ala Gly
145                 150                 155                 160

Gly Ala Gly Gln Gly Gly  Tyr Gly Gly Leu Gly  Ser Gln Gly Ala Gly
                165                 170                 175

Arg Gly Gly Leu Gly Gly  Gln Gly Ala Gly Ala  Ala Ala Ala Ala Ala
            180                 185                 190

Ala Gly Gly Ala Gly Gln  Gly Gly Tyr Gly Gly  Leu Gly Ser Gln Gly
        195                 200                 205

Ala Gly Arg Gly Gly Gln  Gly Ala Gly Ala Ala  Ala Ala Ala Gly
    210                 215                 220
```

-continued

Gly Ala Gly Gln Gly Gly Tyr Gly Gly Leu Gly Ser Gln Gly Ala Gly
225                 230                 235                 240

Gln Gly Gly Tyr Gly Gly Leu Gly Ser Gln Gly Ala Gly Arg Gly Gly
            245                 250                 255

Leu Gly Gly Gln Gly Ala Gly Ala Ala Ala Ala Ala Ala Ala Gly Gly
        260                 265                 270

Ala Gly Gln Gly Gly Leu Gly Gly Gln Gly Ala Gly Gln Gly Ala Gly
    275                 280                 285

Ala Ala Ala Ala Ala Ala Gly Gly Ala Gly Gln Gly Gly Tyr Gly Gly
290                 295                 300

Leu Gly Ser Gln Gly Ala Gly Arg Gly Gly Leu Gly Gly Gln Gly Ala
305                 310                 315                 320

Gly Ala Ala Ala Ala Ala Ala Ala Gly Gly Ala Gly Gln Gly Gly Tyr
            325                 330                 335

Gly Gly Leu Gly Ser Gln Gly Ala Gly Arg Gly Gly Gln Gly Ala Gly
        340                 345                 350

Ala Ala Ala Ala Ala Ala Gly Gly Ala Gly Gln Gly Gly Tyr Gly Gly
        355                 360                 365

Leu Gly Ser Gln Gly Ala Gly Gln Gly Gly Tyr Gly Gly Leu Gly Ser
370                 375                 380

Gln Gly Ala Gly Arg Gly Gly Leu Gly Gly Gln Gly Ala Gly Ala Ala
385                 390                 395                 400

Ala Ala Ala Ala Ala Gly Gly Ala Gly Gln Gly Gly Leu Gly Gly Gln
            405                 410                 415

Gly Ala Gly Gln Gly Ala Gly Ala Ala Ala Ala Ala Ala Ala Gly Ala
        420                 425                 430

Gly Gln Gly Gly Tyr Gly Gly Leu Gly Ser Gln Gly Ala Gly Arg Gly
        435                 440                 445

Gly Leu Gly Gly Gln Gly Ala Gly Ala Ala Ala Ala Ala Ala Ala Gly
    450                 455                 460

Gly Ala Gly Gln Gly Gly Tyr Gly Gly Leu Gly Ser Gln Gly Ala Gly
465                 470                 475                 480

Arg Gly Gly Gln Gly Ala Gly Ala Ala Ala Ala Ala Ala Gly Gly Ala
            485                 490                 495

Gly Gln Gly Gly Tyr Gly Gly Leu Gly Ser Gln Gly Ala Gly Gln Gly
        500                 505                 510

Gly Tyr Gly Gly Leu Gly Ser Gln Gly Ala Gly Arg Gly Gly Leu Gly
        515                 520                 525

Gly Gln Gly Ala Gly Ala Ala Ala Ala Ala Ala Gly Gly Ala Gly Gly
    530                 535                 540

Gln Gly Gly Leu Gly Gly Gln Gly Ala Gly Gln Gly Ala Gly Ala Ala
545                 550                 555                 560

Ala Ala Ala Ala Gly Gly Ala Gly Gln Gly Gly Tyr Gly Gly Leu Gly
            565                 570                 575

Ser Gln Gly Ala Gly Arg Gly Gly Leu Gly Gly Gln Gly Ala Gly Ala
        580                 585                 590

Ala Ala Ala Ala Ala Gly Gly Ala Gly Gln Gly Gly Tyr Gly Gly
        595                 600                 605

Leu Gly Ser Gln Gly Ala Gly Arg Gly Gly Gln Gly Ala Gly Ala Ala
610                 615                 620

Ala Ala Ala Ala Gly Gly Ala Gly Gln Gly Gly Tyr Gly Gly Leu Gly
625                 630                 635                 640

-continued

```
Ser Gln Gly Ala Gly Gln Gly Gly Tyr Gly Gly Leu Gly Ser Gln Gly
                645                 650                 655
Ala Gly Arg Gly Gly Leu Gly Gly Gln Gly Ala Gly Ala Ala Ala Ala
            660                 665                 670
Ala Ala Ala Gly Gly Ala Gly Gln Gly Gly Leu Gly Gly Gln Gly Ala
        675                 680                 685
Gly Gln Gly Ala Gly Ala Ala Ala Ala Ala Gly Gly Ala Gly Gln
    690                 695                 700
Gly Gly Tyr Gly Gly Leu Gly Ser Gln Gly Ala Gly Arg Gly Gly Leu
705                 710                 715                 720
Gly Gly Gln Gly Ala Gly Ala Ala Ala Ala Ala Ala Gly Gly Ala
                725                 730                 735
Gly Gln Gly Gly Tyr Gly Gly Leu Gly Ser Gln Gly Ala Gly Arg Gly
            740                 745                 750
Gly Gln Gly Ala Gly Ala Ala Ala Ala Ala Gly Gly Ala Gly Gln
        755                 760                 765
Gly Gly Tyr Gly Gly Leu Gly Ser Gln Gly Ala Gly Gln Gly Gly Tyr
    770                 775                 780
Gly Gly Leu Gly Ser Gln Gly Ala Gly Arg Gly Gly Leu Gly Gly Gln
785                 790                 795                 800
Gly Ala Gly Ala Ala Ala Ala Ala Ala Gly Gly Ala Gly Gln Gly
                805                 810                 815
Gly Leu Gly Gly Gln Gly Ala Gly Gln Gly Ala Gly Ala Ala Ala Ala
            820                 825                 830
Ala Ala Gly Gly Ala Gly Gln Gly Gly Tyr Gly Gly Leu Gly Ser Gln
        835                 840                 845
Gly Ala Gly Arg Gly Gly Leu Gly Gly Gln Gly Ala Gly Ala Ala Ala
    850                 855                 860
Ala Ala Ala Gly Gly Ala Gly Gln Gly Gly Tyr Gly Gly Leu Gly
865                 870                 875                 880
Ser Gln Gly Ala Gly Arg Gly Gly Gln Gly Ala Gly Ala Ala Ala Ala
                885                 890                 895
Ala Ala Gly Gly Ala Gly Gln Gly Gly Tyr Gly Gly Leu Gly Ser Gln
            900                 905                 910
Gly Ala Gly Gln Gly Gly Tyr Gly Gly Leu Gly Ser Gln Gly Ala Gly
        915                 920                 925
Arg Gly Gly Leu Gly Gly Gln Gly Ala Gly Ala Ala Ala Ala Ala
    930                 935                 940
Ala Gly Gly Ala Gly Gln Gly Gly Leu Gly Gly Gln Gly Ala Gly Gln
945                 950                 955                 960
Gly Ala Gly Ala Ala Ala Ala Ala Gly Gly Ala Gly Gln Gly Gly
                965                 970                 975
Tyr Gly Gly Leu Gly Ser Gln Gly Ala Gly Arg Gly Gly Leu Gly Gly
            980                 985                 990
Gln Gly Ala Gly Ala Ala Ala Ala Ala Ala Gly Gly Ala Gly Gln
        995                 1000                1005
Gly Gly Tyr Gly Gly Leu Gly Ser Gln Gly Ala Gly Arg Gly Gly
    1010                1015                1020
Gln Gly Ala Gly Ala Ala Ala Ala Ala Gly Gly Ala Gly Gln
    1025                1030                1035
Gly Gly Tyr Gly Gly Leu Gly Ser Gln Gly Ala Gly Gln Gly Gly
    1040                1045                1050
Tyr Gly Gly Leu Gly Ser Gln Gly Ala Gly Arg Gly Gly Leu Gly
```

```
                    1055                1060                1065

Gly Gln Gly Ala Gly Ala Ala  Ala Ala Ala Ala  Gly Gly Ala
    1070                1075                1080

Gly Gln Gly Gly Leu Gly Gly  Gln Gly Ala Gly  Gln Gly Ala Gly
    1085                1090                1095

Ala Ala  Ala Ala Ala Ala Gly  Gly Ala Gly Gln  Gly Gly Tyr Gly
    1100                1105                1110

Gly Leu  Gly Ser Gln Gly Ala  Gly Arg Gly Gly  Leu Gly Gly Gln
    1115                1120                1125

Gly Ala  Gly Ala Ala Ala Ala  Ala Ala Gly Gly  Ala Gly Gln
    1130                1135                1140

Gly Gly  Tyr Gly Gly Leu Gly  Ser Gln Gly Ala  Gly Arg Gly Gly
    1145                1150                1155

Gln Gly  Ala Gly Ala Ala Ala  Ala Ala Ala Gly  Gly Ala Gly Gln
    1160                1165                1170

Gly Gly  Tyr Gly Gly Leu Gly  Ser Gln Gly Ala  Gly Gln Gly Gly
    1175                1180                1185

Tyr Gly  Gly Leu Gly Ser Gln  Gly Ala Gly Arg  Gly Gly Leu Gly
    1190                1195                1200

Gly Gln  Gly Ala Gly Ala Ala  Ala Ala Ala Ala  Gly Gly Ala
    1205                1210                1215

Gly Gln  Gly Gly Leu Gly Gly  Gln Gly Ala Gly  Gln Gly Ala Gly
    1220                1225                1230

Ala Ala  Ala Ala Ala Ala Gly  Gly Ala Gly Gln  Gly Gly Tyr Gly
    1235                1240                1245

Gly Leu  Gly Ser Gln Gly Ala  Gly Arg Gly Gly  Leu Gly Gly Gln
    1250                1255                1260

Gly Ala  Gly Ala Ala Ala Ala  Ala Ala Ala Gly  Gly Ala Gly Gln
    1265                1270                1275

Gly Gly  Tyr Gly Gly Leu Gly  Ser Gln Gly Ala  Gly Arg Gly Gly
    1280                1285                1290

Gln Gly  Ala Gly Ala Ala Ala  Ala Ala Ala Gly  Gly Ala Gly Gln
    1295                1300                1305

Arg Gly  Tyr Gly Gly Leu Gly  Ser
    1310                1315

<210> SEQ ID NO 4
<211> LENGTH: 34
<212> TYPE: PRT
<213> ORGANISM: Nephila clavipes
<220> FEATURE:
<221> NAME/KEY: misc_feature
<222> LOCATION: (32)..(34)
<223> OTHER INFORMATION: May or may not be present

<400> SEQUENCE: 4

Gly Gly Ala Gly Gln Gly Gly Tyr Gly Gly Leu Gly Ser Gln Gly Ala
1               5                   10                  15

Gly Arg Gly Gly Leu Gly Gly Gln Gly Ala Gly Ala Ala Ala Ala Ala
            20                  25                  30

Ala Ala

<210> SEQ ID NO 5
<211> LENGTH: 36
<212> TYPE: PRT
<213> ORGANISM: Nephila clavipes
<220> FEATURE:
```

-continued

```
<221> NAME/KEY: misc_feature
<222> LOCATION: (33)..(36)
<223> OTHER INFORMATION: May or may not be present

<400> SEQUENCE: 5

Gly Pro Gly Gly Tyr Gly Pro Gly Gln Gln Gly Pro Gly Gly Tyr Ala
1               5                   10                  15

Pro Gly Gln Gln Pro Ser Gly Pro Gly Ser Ala Ala Ala Ala Ala Ala
            20                  25                  30

Ala Ala Ala Ala
        35

<210> SEQ ID NO 6
<211> LENGTH: 5
<212> TYPE: PRT
<213> ORGANISM: Nephila clavipes
<220> FEATURE:
<221> NAME/KEY: MOD_RES
<222> LOCATION: (5)..(5)
<223> OTHER INFORMATION: Any amino acid

<400> SEQUENCE: 6

Gly Pro Gly Gly Xaa
1               5

<210> SEQ ID NO 7
<211> LENGTH: 5
<212> TYPE: PRT
<213> ORGANISM: Nephila clavipes

<400> SEQUENCE: 7

Gly Pro Gly Gln Gln
1               5

<210> SEQ ID NO 8
<211> LENGTH: 5
<212> TYPE: PRT
<213> ORGANISM: Nephila madagascariensis
<220> FEATURE:
<221> NAME/KEY: MOD_RES
<222> LOCATION: (5)..(5)
<223> OTHER INFORMATION: Any amino acid

<400> SEQUENCE: 8

Gly Pro Gly Gly Xaa
1               5

<210> SEQ ID NO 9
<211> LENGTH: 44
<212> TYPE: PRT
<213> ORGANISM: Nephila sp.

<400> SEQUENCE: 9

Ala Gly Gln Gly Gly Tyr Gly Gly Leu Gly Ser Gln Gly Ala Gly Arg
1               5                   10                  15

Gly Gly Leu Gly Gly Gln Gly Ala Gly Ala Ala Ala Ala Ala Ala Ala
            20                  25                  30

Gly Gly Ala Gly Gln Gly Gly Leu Gly Gly Gln Gly
        35                  40

<210> SEQ ID NO 10
<211> LENGTH: 27
<212> TYPE: PRT
<213> ORGANISM: Nephila sp.
```

```
<400> SEQUENCE: 10

Ala Gly Gln Gly Ala Gly Ala Ser Ala Ala Ala Gly Gly Ala Gly
1               5                   10                  15

Gln Gly Gly Tyr Gly Gly Leu Gly Ser Gln Gly
            20                  25

<210> SEQ ID NO 11
<211> LENGTH: 34
<212> TYPE: PRT
<213> ORGANISM: Nephila sp.

<400> SEQUENCE: 11

Ala Gly Arg Gly Gly Leu Gly Gly Gln Gly Ala Gly Ala Val Ala Ala
1               5                   10                  15

Ala Ala Ala Gly Gly Ala Gly Gln Gly Gly Tyr Gly Gly Leu Gly Ser
            20                  25                  30

Gln Gly

<210> SEQ ID NO 12
<211> LENGTH: 30
<212> TYPE: PRT
<213> ORGANISM: Nephila sp.

<400> SEQUENCE: 12

Ala Gly Arg Gly Gly Gln Gly Ala Gly Ala Ala Ala Ala Ala Ala Gly
1               5                   10                  15

Gly Ala Gly Gln Arg Gly Tyr Gly Gly Leu Gly Asn Gln Gly
            20                  25                  30

<210> SEQ ID NO 13
<211> LENGTH: 20
<212> TYPE: PRT
<213> ORGANISM: Nephila sp.

<400> SEQUENCE: 13

Gly Pro Gly Gly Tyr Gly Pro Gly Gln Gln Gly Pro Gly Ala Ala Ala
1               5                   10                  15

Ala Ala Ser Ala
            20

<210> SEQ ID NO 14
<211> LENGTH: 24
<212> TYPE: PRT
<213> ORGANISM: Nephila sp.

<400> SEQUENCE: 14

Gly Arg Gly Pro Gly Gly Tyr Gly Pro Gly Gln Gln Gly Pro Gly Gly
1               5                   10                  15

Ser Gly Ala Ala Ala Ala Ala Ala
            20

<210> SEQ ID NO 15
<211> LENGTH: 25
<212> TYPE: PRT
<213> ORGANISM: Nephila sp.

<400> SEQUENCE: 15

Gly Ser Gly Pro Gly Gly Tyr Gly Pro Gly Gln Gln Gly Pro Gly Gly
1               5                   10                  15

Pro Gly Ala Ala Ala Ala Ala Ala Ala
            20                  25
```

-continued

<210> SEQ ID NO 16
<211> LENGTH: 29
<212> TYPE: PRT
<213> ORGANISM: Nephila sp.

<400> SEQUENCE: 16

Gly Arg Gly Pro Gly Gly Tyr Gly Pro Gly Gln Gln Gly Pro Gly Gln
1               5                   10                  15

Gln Gly Pro Gly Gly Ser Gly Ala Ala Ala Ala Ala Ala
            20                  25

<210> SEQ ID NO 17
<211> LENGTH: 24
<212> TYPE: PRT
<213> ORGANISM: Nephila sp.

<400> SEQUENCE: 17

Gly Arg Gly Pro Gly Gly Tyr Gly Pro Gly Gln Gln Gly Pro Gly Gly
1               5                   10                  15

Pro Gly Ala Ala Ala Ala Ala Ala
            20

<210> SEQ ID NO 18
<211> LENGTH: 20
<212> TYPE: PRT
<213> ORGANISM: Nephila sp.

<400> SEQUENCE: 18

Gly Pro Gly Gly Tyr Gly Pro Gly Gln Gln Gly Pro Gly Ala Ala Ala
1               5                   10                  15

Ala Ala Ala Ala
            20

<210> SEQ ID NO 19
<211> LENGTH: 24
<212> TYPE: PRT
<213> ORGANISM: Nephila sp.

<400> SEQUENCE: 19

Gly Ser Gly Ala Gly Gly Tyr Gly Pro Gly Gln Gln Gly Pro Gly Gly
1               5                   10                  15

Pro Gly Ala Ala Ala Ala Ala Ala
            20

<210> SEQ ID NO 20
<211> LENGTH: 24
<212> TYPE: PRT
<213> ORGANISM: Nephila sp.

<400> SEQUENCE: 20

Gly Ser Gly Pro Gly Gly Tyr Gly Pro Gly Gln Gln Gly Pro Gly Gly
1               5                   10                  15

Ser Ser Ala Ala Ala Ala Ala Ala
            20

<210> SEQ ID NO 21
<211> LENGTH: 26
<212> TYPE: PRT
<213> ORGANISM: Nephila sp.

<400> SEQUENCE: 21

```
Gly Ser Gly Pro Gly Tyr Gly Pro Gln Gln Gly Pro Gly Gly
1               5                   10                  15

Ser Gly Ala Ala Ala Ala Ala Ala Ala
            20                  25

<210> SEQ ID NO 22
<211> LENGTH: 24
<212> TYPE: PRT
<213> ORGANISM: Nephila sp.

<400> SEQUENCE: 22

Gly Arg Gly Pro Gly Gly Tyr Gly Gln Gly Gln Gln Gly Pro Gly Gly
1               5                   10                  15

Pro Gly Ala Ala Ala Ala Ala Ala
            20

<210> SEQ ID NO 23
<211> LENGTH: 27
<212> TYPE: PRT
<213> ORGANISM: Latrodectus hesperus

<400> SEQUENCE: 23

Gly Gly Ala Gly Gln Gly Gly Tyr Gly Arg Gly Gly Ala Gly Gln Gly
1               5                   10                  15

Gly Ala Gly Ala Ala Ala Ala Ala Ala Ala
            20                  25

<210> SEQ ID NO 24
<211> LENGTH: 24
<212> TYPE: PRT
<213> ORGANISM: Latrodectus hesperus

<400> SEQUENCE: 24

Gly Gly Ala Gly Pro Gly Arg Gln Gln Gly Tyr Gly Pro Gly Ser Ser
1               5                   10                  15

Gly Ala Ala Ala Ala Ala Ala Ala
            20

<210> SEQ ID NO 25
<211> LENGTH: 51
<212> TYPE: PRT
<213> ORGANISM: Nephila clavipes

<400> SEQUENCE: 25

Gly Ala Gly Ala Gly Ala Gly Ala Ala Ala Gly Ala Gly Ala Gly Ala
1               5                   10                  15

Gly Gly Ala Gly Tyr Gly Gly Gln Gly Gly Tyr Gly Ala Gly Ala Gly
            20                  25                  30

Ala Gly Ala Ala Ala Ala Gly Ala Gly Ala Gly Ala Gly Gly
        35                  40                  45

Tyr Gly Arg
    50

<210> SEQ ID NO 26
<211> LENGTH: 23
<212> TYPE: PRT
<213> ORGANISM: Nephila clavipes

<400> SEQUENCE: 26

Gly Ala Gly Val Gly Ala Gly Ala Ala Ala Gly Phe Ala Ala Gly Ala
1               5                   10                  15
```

Gly Gly Ala Gly Gly Tyr Arg
             20

<210> SEQ ID NO 27
<211> LENGTH: 411
<212> TYPE: PRT
<213> ORGANISM: Nephila madagascariensis

<400> SEQUENCE: 27

Ile Ser Glu Glu Leu Thr Ile Gly Gly Ala Gly Ala Gly Gly Val Gly
1               5                   10                  15

Pro Gly Gly Ser Gly Pro Gly Gly Val Gly Pro Gly Gly Ser Gly Pro
            20                  25                  30

Gly Gly Val Gly Pro Gly Gly Ser Gly Pro Gly Gly Val Gly Ser Gly
            35                  40                  45

Gly Ser Gly Pro Gly Gly Val Gly Pro Gly Gly Ser Gly Pro Gly Gly
            50                  55                  60

Val Gly Ser Gly Gly Phe Gly Pro Gly Gly Ile Gly Pro Gly Gly Ser
65                  70                  75                  80

Gly Pro Gly Gly Val Gly Pro Gly Gly Val Gly Pro Tyr Gly Pro
            85                  90                  95

Gly Gly Ser Gly Pro Gly Gly Ala Gly Gly Ala Gly Ser Tyr Gly
            100                 105                 110

Pro Gly Gly Pro Tyr Gly Pro Gly Gly Ser Gly Pro Gly Gly Ala
            115                 120                 125

Gly Gly Pro Tyr Gly Pro Gly Gly Ala Gly Gly Pro Tyr Gly Pro Gly
            130                 135                 140

Gly Pro Tyr Gly Pro Gly Gly Ala Gly Pro Gly Gly Glu Gly Pro
145                 150                 155                 160

Gly Gly Ala Gly Gly Pro Tyr Gly Pro Gly Gly Pro Gly Ala Gly
            165                 170                 175

Pro Gly Gly Tyr Gly Pro Gly Gly Ala Gly Pro Gly Gly Tyr Gly Pro
            180                 185                 190

Gly Gly Ala Gly Pro Gly Gly Tyr Gly Pro Gly Gly Ala Gly Ser Gly
            195                 200                 205

Gly Tyr Gly Pro Gly Gly Ala Gly Pro Gly Gly Tyr Gly Pro Gly Gly
            210                 215                 220

Pro Gly Pro Gly Gly Tyr Gly Pro Gly Gly Ala Gly Pro Gly Gly Tyr
225                 230                 235                 240

Gly Pro Gly Gly Thr Gly Pro Gly Gly Ser Ala Pro Gly Gly Ala Gly
            245                 250                 255

Pro Gly Gly Ala Gly Pro Gly Gly Tyr Gly Pro Gly Gly Ser Gly Pro
            260                 265                 270

Gly Gly Tyr Gly Pro Gly Gly Pro Gly Gly Ala Gly Pro Gly Gly
            275                 280                 285

Ala Gly Pro Gly Gly Ala Gly Pro Gly Gly Ala Gly Pro Gly Gly Ala
            290                 295                 300

Gly Pro Gly Gly Ala Gly Pro Gly Gly Ala Gly Pro Gly Gly Ala Gly
305                 310                 315                 320

Pro Gly Gly Ala Gly Pro Gly Gly Ala Gly Pro Gly Gly Val Gly Thr
            325                 330                 335

Gly Gly Leu Gly Arg Gly Gly Ala Gly Arg Gly Gly Ala Gly Arg Gly
            340                 345                 350

Gly Ala Gly Arg Gly Gly Ala Gly Arg Gly Gly Ala Gly Arg Gly Gly
            355                 360                 365

Thr Gly Gly Val Gly Gly Ala Gly Gly Ala Gly Ala Gly Gly Val
    370                 375                 380

Gly Gly Ala Gly Gly Ser Gly Gly Thr Thr Val Ile Glu Asp Leu Asp
385                 390                 395                 400

Ile Thr Ile Asp Gly Ala Asp Gly Pro Ile Thr
            405                 410

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ataccatgga acatcatcat catcatcatg gaggcatgca gatcttcgtc aagactttga    60

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
actggatcca cctcttagcc ttagcacaac                                     30

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atatccatgg aaaagagatc tgactcagaa gtcaatcaag aa                       42

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cttgaagaaa atctctgaa                                                 19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttcagagatt ttcttcaag                                                 19

<210> SEQ ID NO 33
<211> LENGTH: 34
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 33
atatcaattg gatccaccaa tctgttctct gtga                                 34

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgcatggat cc                                                         12
```

METHOD FOR PRODUCING WEB PROTEIN, A FUSED PROTEIN, RECOMBINANT DNA, AN EXPRESSION VECTOR, A HOST CELL AND STRAIN-PRODUCERS

TECHNICAL FIELD

The invention relates to biotechnologies and provides a method for producing recombinant proteins from the orb weaving spider silk, fused proteins comprising sequences of recombinant proteins from the orb weaving spider silk and sequences of ubiquitin-like proteins, recombinant DNAs encoding fused proteins, yeast host cells, and expression vectors suitable for carrying out the method, as well as producer strains of recombinant proteins from the orb weaving spider silk.

SEQUENCE LISTING

The instant application contains a Sequence Listing which has been submitted in ASCII format via EFS-Web and is hereby incorporated by reference in its entirety. Said ASCII copy, created on Oct. 14, 2015, is named 5959-104US (89661)_SL.txt and is 49,149 bytes in size.

PRIOR ART

Spider silk is a unique biomaterial wherein amazing strength is combined with elasticity. It is unparalleled is this respect both among natural and man-made materials. Thus, for example, the dragline silk of *Nephila clavipes* orb weaving spiders exceeds steel and is comparable to Kevlar in terms of the tensile strength values and even exceeds Kevlar in terms of the tensile energy values; at the same time, it is stretchable by up to 35% of its length [Gosline J. M. et al. Endeavor, 1986, v. 10, 37-43].

Such materials may be obtained in commercial quantities only using gene engineering and biotechnological techniques. At present, a number of genes encoding spider silks have been isolated and characterized completely enough [Xu M. & Lewis R. Proc. Natl. Acad. Sci., USA, 1990, v. 87, 7120-7124; Hinnman M. & Lewis R. J. Biol. Chem., 1992, v. 267, 19320-19324; Guerette P. et al. J. Science, 1996, v. 272, 112-115; Hayashi C. Y. & Lewis R. V. J. Mol. Biol., 1998, v. 275, 773-784]. These genes belong to the most lengthy of the known cistrons (mRNA sizes vary from 7.5 to 15.5 thousand nucleotides) and consist of a large number of tandem repeating lengthy sequences notably differing in various genes. The most well-studied dragline silk of the *Nephila clavipes* orb weaving spiders consists of two proteins, spidroin 1 and spidroin 2 (MaSp1 and MaSp2, respectively) of the major ampullate gland [Hinnman M. & Lewis R. J. Biol. Chem., 1992, v. 267, 19320-19324; Guerette P. et al. Science, 1996, v. 272, 112-115]. The spidroin 1 repetitive sequence may be presented as the following consensus sequence:

[GGAGQGGYGGLGSQGAGRGGLGGQGAG(A)$_{4-7}$]
(SEQ ID NO: 4), and the spidroin 2 repetitive sequence as:
[GPGGYGPGQQGPGGYAPGQQPSGPGS(A)$_{6-10}$]
(SEQ ID NO: 5)

A vital difference between these proteins consists in that in case of spidroin 1 the elementary repeat is GGX tripeptide (X=A, S or Y) while in case of spidroin 2—GPGGX (SEQ ID NO: 6) and GPGQQ (SEQ ID NO: 7) pentapeptides. At the same time, spidroin 1 is characterized by an increased strength while spidroin 2 able to form β-helices [Hayashi et al., 1999, Int. J. Biol. Macromol., v. 24, 271-275] by a high elasticity. The unique combination of properties of the dragline silk is due precisely to the interaction between these proteins.

The MiSp1 and MiSp2 proteins of the minor ampullate gland and the Flag protein found in the net silk of orb weaving spiders also have a repetitive structure. The repetitive regions are enriched with alanine and glycine. GGX and GA motifs are presented along the whole length of the amino acid sequence of both MiSp1 and MiSp2 [K. Vasanthavada et al. Cell. Mol. Life Sci, 2006, v. 63, 1986-1999]. In the Flag sequence, dominant repetitive motifs are presented by GPGGX (SEQ ID NO: 8) pentapeptide and GGX tripeptide.

Based on the studies of the proteins found in the dragline silk of *Nephila clavipes* orb weaving spiders as well as the proteins of the net silk and proteins of the minor ampullate gland [Kohler T. & Vollrath F. J. Exp. Zool., 1995, v. 271, 1-17; Colgin M. A. & Lewis R., Protein Sci., 1998, v. 7, 667-672], a modular hypothesis of the silk proteins has been proposed [Hinman at al., 2000, *TIBTECH*, v. 1, 374-379]. The structural analysis of the silk proteins shows that there are crystalline regions present therein, formed by β-folded structures (believed to be formed by $(A)_n$ and $(GA)_n$ blocks) which ensure the strength of the silk threads and which are submersed into a less structured Gly-enriched matrix responsible for elasticity. Non-repetitive (NR) unique conservative sequences are found at ends of molecules, said sequences being presumably necessary to improve the solubility of proteins in the concentrated solution within the gland and also to correctly align molecules when a thread is formed during spinning.

Attempts have bee made to clone and optimize in *E. coli* cells the expression of cDNA-copies of natural genes encoding the dragline silk proteins [Arcidiacono S. et al. Appl. Microbiol. Biotechnol., 1998, v. 49, 1-38]. However, the level of expression achieved was rather low, which is due first of all to a mismatch between the frequencies of occurrence of certain amino acid codons in the spider genes and in the genes of a recipient microorganism used.

It proved to be more successful to apply chemical-fermentative synthesis of the silk protein genes followed by cloning in bacteria, yeast, tobacco, potato cells using synthetic DNA modules with a frequency of use of codons adapted to the respective host cell [Prince J. T. et al. Biochemistry, 1995, v. 34, 10879-10884; Winkler S. et al. Int. J. Biol. Macromol, 1999, v. 24, 265-270; Fahnestock S. R. & Bedzyk L. A. Appl. Microbiol. Biotechnol, 1997, v. 47, 33-39; Fahnestock S. R. & Irwin S. L., Appl. Microbiol. Biotechnol., 1997, v. 47, 23-32; Lewis, R. V. et al., 1996, Protein Expr. Purif., v. 7, 400-406; Scheller, J. et al., 2001, Nat. Biotechnol., v. 19, 573-577]. The above studies are mainly related to the expression of genes encoding recombinant proteins of the orb weaving spider dragline silk, containing a consensus sequence or small fragments thereof. Expression of synthetic genes resulted in artificial proteins containing variants of primary repeats in spidroins 1 and 2, similar to repetitive regions in natural proteins. While these proteins exhibited the properties of a secondary structure typical for silk proteins, the threads produced on the basis thereof were far inferior to the natural silk threads in terms of their mechanical properties. None of those artificial proteins comprised C-terminal NR-regions found in all dragline silk proteins. The artificial analogs with the properties closest to those of natural proteins comprised 800 and 1600 amino acid residues and resulted from the expression of synthetic genes in *E. coli* cells [Fahnestock & Irwin, 1997, Appl. Microbiol. Biotechnol., v. 47, 23-32] or *Pichia*

*pastoris* yeast [Fahnestock & Bedzyk, 1997, Appl. Microbiol. Biotechnol, v. 47, 33-39].

As a first step to study the molecular mechanisms of the silk threads assembly, the primary structure of ADF-3 and ADF-4 proteins found in the dragline silk of the garden spiders (*Araneus diadematus*) corresponding to the MaSp2 and MaSp1 proteins (spidroins 2 and 1 of the major ampullate gland) has been analyzed. Recombinant spider silks consisting of synthetic repetitive sequences and unique authentic NR-regions at the molecule ends have been expressed in *E. coli* cells to yield the refined protein of about 1 g per liter of the bacterial culture [WO/2006/008163].

The comparative analysis of the secondary structure, solubility and aggregation properties of the obtained proteins was performed to identify the role of various elements of the silk protein primary structure. It has been found that the solubility of synthetic proteins is determined by repetitive regions constituting the major part of the silk proteins lengthwise and comprising a consensus sequence including a poly-A block with the alternation of hydrophobic and hydrophilic segments in the primary repeats being important to enable the solubility.

Non-repetitive C-terminal regions play an important role in the initiation of the protein assembly. Two modules have been used in this expression system as synthetic building blocks: a poly-A module and a second module consisting of four GPGQQ repeats. Such type of modules is also disclosed by Hummerich et al. [Hummerich, D. et al., 2004, Biochemistry, v. 43, 13604-13612].

The silk assembly process has been studied on the models of two recombinant analogs of spidroin 1 (1F9 protein) and spidroin 2 (2E12 protein), forming part of the dragline silk threads of the *Nephila clavipes* and *Nephila madagascariensis* spiders, respectively [Bogush V. G. & Debabov V. G., 2009, J. Neuroimmune Pharmacol., v. 4, 17-27].

The 1F9 synthetic gene has been expressed in *Saccharomyces cerevisiae* yeast under control of the GAL1 promotor using a bireplicon expression vector [Bogush V. G. at al., 2001, Biotechnologies, V. 2, 11-22] and in the cells of *Pichia pastoris* methylotrophic yeast under control of the AOX I methnol-inducible promotor using the pHIL-D2 integrative vector [Bogush V. G. at al., 2006, Biotechnologies, V. 4, 3-12].

In the first case, more than 80% of the target protein was found in the water insoluble fracture with the average yield of 6-8 mg of protein per 1 liter of the fermentative yeast culture. In *Pichia pastoris*, the average yield of the pure 1F9 was approximately 70 mg per 1 kg of the humid cell mass (approximately 23 mg/l of the fermentative culture). The sequences of recombinant proteins were approximated as much as possible to the sequences of natural proteins, in particular the repetitive region of the 1F9 comprised 9 repeats of a "monomer" consisting of five versions of the primary repeats found in the natural spidroine 1. In order to increase the level of the recombinant protein synthesis in the yeast cells, the structure of the 1f9 and 2E12 genes has been modified by replacing "rare" triplets with codons typical for the effectively expressing yeast genes, and the number of internal repeats of nucleotide sequences has been minimized. As a result of the chemical-fermentative synthesis, DNA fragments encoding the respective monomers in both proteins have been obtained and then amplified. The final 1F9 gen encoded nine repeats of the respective "monomer", forming a protein with a molecular weight of 94 kDa; the 2E12 protein (113 kDa) comprised 12 "monomeric" repeats.

Structural transitions arising under certain exposure have been investigated in the solutions of the 1F9 and 2E12 proteins treated by cation-exchange chromatography [Bogush V. G. & Debabov V. G., 2009, J. Neuroimmune Pharmacol., v. 4, 17-27]. Despite the absence of hydrophilic N- and C-terminal unique sequences (NR) which as believed before are required to form nanofibrils and micelles, nanofibrils of 100 nm to 1 µm in length and micelles of 1 µm in diameter were spontaneously formed by the two proteins in an aqueous solution. In addition, the nanofibrils had a spiral structure with a period of 40 nm.

However, the level of synthesis of the spider silk recombinant proteins using the known methods prevents from obtaining the spider silks in the quantities sufficient not only for studying their structure and properties but also for developing and testing a new class of medical materials and articles made from the same. A method for increasing the expression of a poorly expressing protein by the gene engineering techniques comprises biosynthesis thereof in the form of a hybrid protein wherein the target protein is fused with the effectively expressing protein [Shatzman and Rosenberg, 1987, Methods Enzynol., v. 152, 661-673]. However, the advantages of such approach are to a great extent renderer null by the necessity to perform processing of the hybrid product at the closing stages of treatment in order to release the target protein from the same, which is practically unfeasible in case of the spider silk recombinant proteins. It has been shown, that the yeast ubiquitin used as an effectively expressing component causes the hybrids to undergo a highly specific intracellular processing in the yeast cells. The yeast ubiquitin consisting of 76 amino acid residues is a representative of the family of ubiquitin-like eukaryote proteins to which relatively small structurally conservative proteins belong, exhibiting an extraordinary convolution rate, high solubility and thermal stability; in vivo proteins of this family serve for a reversible modification and alteration of the functional status of other proteins. Ubiquitin-like proteins contain a conservative C-terminal Gly-Gly motif being a processing site [Müller et al., 2001, Nature, v. 2, 202-210]. The presence of this site within the hybrid proteins with ubiquitin results in that the hybrids undergo a high specific intracellular processing in the yeast cells under the action of ubiquitin-specific DUB proteinases so that the ubiquitin component is absent in the final expression products.

It has been found later that apart from ubiquitin, other proteins of the ubiquitin family may be also used to enhance the expression, in particular, a yeasty variant of the SUMO protein. Mature SUMO protein of *Saccharomyces cerevisiae* yeast encoded by unique SMT3 gen (Johnson et al., 1997, EMBO J, v. 16, 5509-5519; Muller et al., 1998, EMBO J, v. 17, 61-70) comprises 98 amino acid residues of which residues 13-98 are relevant to form its native structure [Mossessova E. & Lima C. D., 2000, Mol. Cell, v. 5, 865-876]. Similar to ubiquitin-specific proteinases, SUMO-specific yeast proteinases provide a high efficiency and specificity of processing of the SUMO-containing hybrid proteins [Malakhov et al., 2004, J. Struct. Funct. Genom., v. 5, 75-86; Butt et al., 2005, Protein Expr. Purif., v. 43, 1-9].

However, the efficiency of hybridizing the spider silk recombinant proteins with ubiquitin or other ubiquitin-like proteins to enhance the biosynthesis of the silk proteins has not been shown.

Therefore, a need still exists for providing a method for microbiological biosynthesis to considerably increase the production of the spider silk recombinant proteins with the properties close to the properties of natural proteins whereby a possibility in principle would be opened to provide biomaterials with unique properties based on the spider silk recombinant proteins.

SUMMARY OF THE INVENTION

A method is provided for producing the recombinant proteins of the orb weaving spider silk in the yeast cells, said method enabling a production of recombinant proteins tens of times exceeding the production of the spider silk recombinant proteins available according to the methods known in the prior art.

According to the inventive method, the recombinant proteins of the orb weaving spider silk express in the yeast cells in the form of a hybrid with a ubiquitin-like protein occupying an N-terminal position within the hybrid and comprising a processing site recognizable by natural yeast proteinases, preferably, ubiquitin-specific DUB proteinases or SUMO-specific yeast proteinases so that hybrid proteins undergo processing under the action of proteinases in the course of expression to enable accumulation in the yeast cells of the mature spider silk protein free of the hybrid component, wherein the protein is accumulated in the water insoluble fraction of the yeast cells.

Preferably, the method according to the invention comprises obtaining a spider silk recombinant protein whose consensus sequences are derived from the dragline silk proteins of the major ampullate gland and/or proteins of the minor ampullate gland or from the net silk protein of the orb weaving spiders.

In a preferred embodiment, the method according to the invention comprises obtaining spider silk recombinant proteins, whose consensus sequences are derived from the dragline silk proteins of the major ampullate gland of *Nephila clavipes* and/or *Nephila madagascariensis*, and the ubiquitin-like protein is selected from the group including ubiquitin and *Saccharomyces cerevisiae* SUMO protein.

In one of the most preferred embodiments, the method according to the invention comprises obtaining the recombinant 2E12 protein of the *Nephila madagascariensis* orb weaving spider dragline silk in the cells of *Saccharomyces cerevisiae* under control of the GAL1 gene yeast promotor, wherein the recombinant protein gene is fused with the sequence encoding ubiquitin or *Saccharomyces cerevisiae* SUMO protein.

In another most preferred embodiment, the method according to the invention comprises expressing the gene of the recombinant 1F9 protein of *Nephila clavipes* orb weaving spider dragline silk in the cells of *Saccharomyces cerevisiae* under control of the GAL1 gene yeast promotor, wherein the recombinant protein gene is fused with the sequence encoding ubiquitin or *Saccharomyces cerevisiae* SUMO protein.

In one aspect, the invention provides a fused protein comprising the sequences of a spider silk recombinant protein of orb weaving spiders and a ubiquitin-like protein occupying an N-terminal position with respect to the spider silk recombinant protein within the fused protein, wherein the sequence of the spider silk recombinant protein comprises consensus sequences derived from repetitive sequences of the MaSp1 and MaSp2 proteins of the major ampullate gland dragline silk, MiSp1 and MiSp2 proteins of the minor ampullate gland and Flag protein of orb weaving spider net silk.

In a preferred embodiment, the invention provides a fused protein wherein a ubiquitin-like protein comprises ubiquitin or *Saccharomyces cerevisiae* SUMO protein, and the sequence of the spider silk recombinant protein comprises consensus sequences derived from repetitive sequences of the MaSp1 and MaSp2 proteins of the *Nephila clavipes* and *Nephila madagascariensis* major ampullate gland dragline silk and selectable from the group of:

```
                                          (SEQ ID NO: 9)
AGQGGYGGLGSQGAGRGGLGGQGAGAAAAAAAGGAGQGGLGGQG (SEQ ID NO: 10)
AGQGAGASAAAAGGAGQGGYGGLGSQG (SEQ ID NO: 11)
AGRGGLGGQGAGAVAAAAAGGAGQGGYGGLGSQG (SEQ ID NO: 12)
AGRGGQGAGAAAAAAGGAGQRGYGGLGNQG (SEQ ID NO: 13)
GPGGYGPGQQGPGAAAAASA (SEQ ID NO: 14)
GRGPGGYGPGQQGPGGSGAAAAAA (SEQ ID NO: 15)
GSGPGGYGPGQQGPGGPGAAAAAAA (SEQ ID NO: 16)
GRGPGGYGPGQQGPGQQGPGGSGAAAAAA (SEQ ID NO: 17)
GRGPGGYGPGQQGPGGPGAAAAAA (SEQ ID NO: 18)
GPGGYGPGQQGPGAAAAAAA (SEQ ID NO: 19)
GSGAGGYGPGQQGPGGPGAAAAAA (SEQ ID NO: 20)
GSGPGGYGPGQQGPGGSSAAAAAA (SEQ ID NO: 21)
GSGPGGYGPGQQGPGGSGAAAAAAAA (SEQ ID NO: 22)
GRGPGGYGQGQQGPGGPGAAAAAA.
```

Most preferably, a fused protein comprises the recombinant 1F9 protein of the *Nephila clavipes* orb weaving spider dragline silk, whose sequence is fused with the sequence encoding ubiquitin or *Saccharomyces cerevisiae* SUMO protein.

In another most preferred embodiment, a fused protein comprises the recombinant 2E12 protein of the *Nephila madagascariensis* orb weaving spider dragline silk, whose sequence is fused with the sequence encoding ubiquitin or *Saccharomyces cerevisiae* SUMO protein.

In one aspect, the invention provides a recombinant DNA encoding a fused protein comprising a recombinant protein of the orb weaving spider silk and an ubiquitin-like protein occupying an N-terminal position with respect to the spider silk recombinant protein within the fused protein, wherein the sequence of the spider silk recombinant protein comprises consensus sequences derived from repetitive sequences of the MaSp1 and MaSp2 proteins of the major ampullate gland dragline silk, MiSp1 and MiSp2 proteins of the minor ampullate gland and orb weaving spider net silk protein.

Preferably, a recombinant DNA encodes a fused protein wherein the ubiquitin-like protein comprises ubiquitin or *Saccharomyces cerevisiae* SUMO protein, and the sequence of the orb weaving spider silk recombinant protein comprises consensus sequences derived from repetitive sequences of MaSp1 and MaSp2 proteins of the major *Nephila clavipes* and *Nephila madagascariensis* ampullate gland and selectable from the group of:

(SEQ ID NO: 9)
AGQGGYGGLGSQGAGRGGLGGQGAGAAAAAAGGAGQGGLGGQG (SEQ ID NO: 10)
AGQGAGASAAAAGGAGQGGYGGLGSQG (SEQ ID NO: 11)
AGRGGLGGQGAGAVAAAAAGGAGQGGYGGLGSQG (SEQ ID NO: 12)
AGRGGQGAGAAAAAAGGAGQRGYGGLGNQG (SEQ ID NO: 13)
GPGGYGPGQQGPGAAAAASA (SEQ ID NO: 14)
GRGPGGYGPGQQGPGGSGAAAAAA (SEQ ID NO: 15)
GSGPGGYGPGQQGPGGPGAAAAAAA (SEQ ID NO: 16)
GRGPGGYGPGQQGPGQQGPGGSGAAAAAA (SEQ ID NO: 17)
GRGPGGYGPGQQGPGGPGAAAAAA (SEQ ID NO: 18)
GPGGYGPGQQGPGAAAAAAA (SEQ ID NO: 19)
GSGAGGYGPGQQGPGGPGAAAAAA (SEQ ID NO: 20)
GSGPGGYGPGQQGPGGSSAAAAAA (SEQ ID NO: 21)
GSGPGGYGPGQQGPGGSGAAAAAAAA (SEQ ID NO: 22)
GRGPGGYGQGQQGPGGPGAAAAAA.

Most preferably, a recombinant DNA according to the invention encodes a fused protein including the sequences of the recombinant 1F9 protein of the *Nephila clavipes* orb weaving spider dragline silk and ubiquitin or *Saccharomyces cerevisiae* SUMO protein and comprising a sequence from the Listing of Sequences:

(SEQ ID NO:1 and SEQ ID NO:3, respectively).

In another most preferred embodiment, a recombinant DNA encodes a fused protein including the sequences of the recombinant 2E12 protein of the *Nephila madagascariensis* orb weaving spider dragline silk and ubiquitin or *Saccharomyces cerevisiae* SUMO protein.

In one aspect, the invention provides expression vectors comprising DNA sequences which encode recombinant proteins of the orb weaving spider silk, fused with an ubiquitin-like protein gen sequence, occupying an N-terminal position within the fused protein with respect to the spider silk recombinant protein, and the sequences of highly efficient controllable yeast promotors.

In a preferred embodiment, the invention provides an expression vector comprising a recombinant DNA encoding a fused protein wherein an ubiquitin-like protein comprises ubiquitin or *Saccharomyces cerevisiae* SUMO protein, and a sequence of the spider silk recombinant protein comprises consensus sequences derived from repetitive sequences of the MaSp1 and MaSp2 proteins of the *Nephila clavipes* and *Nephila madagascariensis* major ampullate gland of and selectable from the group of:

(SEQ ID NO: 9)
AGQGGYGGLGSQGAGRGGLGGQGAGAAAAAAGGAGQGGLGGQG (SEQ ID NO: 10)
AGQGAGASAAAAGGAGQGGYGGLGSQG (SEQ ID NO: 11)
AGRGGLGGQGAGAVAAAAAGGAGQGGYGGLGSQG (SEQ ID NO: 12)
AGRGGQGAGAAAAAAGGAGQRGYGGLGNQG (SEQ ID NO: 13)
GPGGYGPGQQGPGAAAAASA (SEQ ID NO: 14)
GRGPGGYGPGQQGPGGSGAAAAAA (SEQ ID NO: 15)
GSGPGGYGPGQQGPGGPGAAAAAAA (SEQ ID NO: 16)
GRGPGGYGPGQQGPGQQGPGGSGAAAAAA (SEQ ID NO: 17)
GRGPGGYGPGQQGPGGPGAAAAAA (SEQ ID NO: 18)
GPGGYGPGQQGPGAAAAAAA (SEQ ID NO: 19)
GSGAGGYGPGQQGPGGPGAAAAAA (SEQ ID NO: 20)
GSGPGGYGPGQQGPGGSSAAAAAA (SEQ ID NO: 21)
GSGPGGYGPGQQGPGGSGAAAAAAAA (SEQ ID NO: 22)
GRGPGGYGQGQQGPGGPGAAAAAA.

In one of the most preferred embodiments, the invention provides an expression vector comprising pPDX3-HUB-2E12 bireplicon vector comprising a replication initiation point of an endogenic 2-μm yeast plasmid, a GAL1 gene yeast promotor region, a DNA sequence encoding the recombinant 2E12 protein, fused with a sequence encoding *Saccharomyces cerevisiae* ubiquitin.

In another most preferred embodiment, the invention provides an expression vector comprising pPDX3-HUB-1F9 bireplicon vector comprising a replication initiation point of an endogenic 2-μm yeast plasmid, a GAL1 gene yeast promotor region, a DNA sequence, encoding recombinant 1F9 protein, fused with a sequence encoding *Saccharomyces cerevisiae* ubiquitin.

In another most preferred embodiment, the invention provides an expression vector, comprising pPDX3-SUMO-1F9 bireplicon vector, comprising a replication initiation point of an endogenic 2-μm yeast plasmid, a GAL1 gene yeast promotor region, a DNA sequence, encoding recombinant 1F9 protein, fused with a sequence encoding *Saccharomyces cerevisiae* SUMO protein.

According to another aspect, the invention provides yeast host cells producing the recombinant proteins of the orb weaving spider silk. The most preferred host cells according to the invention are the cells of *Saccharomyces cerevisisae*. In another aspect, the invention provides producer strains of the recombinant 1F9 and 2E12 proteins of the orb weaving spider dragline silk.

EMBODIMENT OF THE INVENTION

Figure 1:
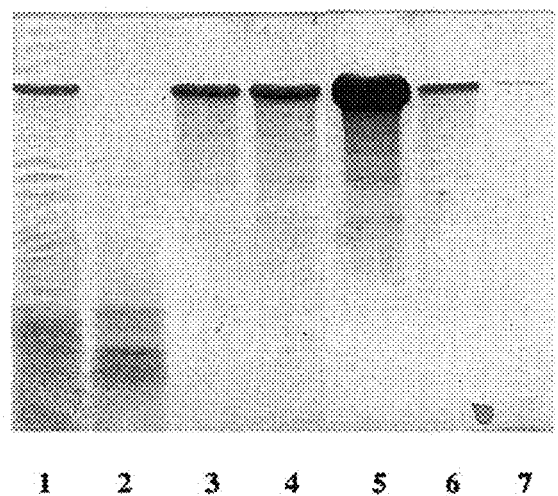
FIG. 1 shows electrophoresis in 12% polyacrylamide gel with DDS-Na of 1F9 fractions after chromatography in the HiPrep 16/10 SP FF cation-exchange column; tracks: 1—original solution before application onto the column; 2—breakthrough fraction; 3-6—fractions containing 1F9 protein, 7—standard 1F9 sample.

The present invention is based on a surprising discovery that the expression of a recombinant protein of the orb weaving spider silk in the yeast cells in the form of a protein fused with a ubiquitin-like protein occupying a N-terminal position within the hybrid, makes it possible to increase tens of times the production of the spider silk recombinant protein, wherein the recombinant protein expressed in the form of a hybrid protein is accumulated in the yeast cells in the water insoluble fractions as a processed protein free of the hybrid component.

Accordingly, in one aspect of the present invention a method is provided for producing the orb weaving spider silk recombinant protein in the yeast cells, comprising constructing an expression vector, transforming the yeast cells by the produced expression vector, and expressing the gen of the orb weaving spider silk recombinant protein in the transformed cells, characterized in that an expression vector is used which includes a DNA sequence encoding a recombinant protein of the orb weaving spider silk, fused with a sequence encoding a ubiquitin-like protein occupying an N-terminal position with respect to the spider silk recombinant protein within the fused protein and comprising a processing site recognizable by the natural yeast proteinases, preferably, by ubiquitin-specific DUB proteinases or SUMO-specific yeast proteinases, so that hybrid proteins undergo processing under the action of proteinases in the course of expression and the spider silk recombinant protein is accumulated in the yeast cells in the water insoluble fractions as a processed protein free of the hybrid component.

The recombinant proteins obtained by the method according to the invention exhibit a pronounced periodic structure which may by presented as a series of consensus sequences derived by equalizing the repeating units of the natural proteins of the orb weaving spider silk. The recombinant proteins according to the invention comprise proteins whose sequences contain both the repeats in one consensus sequence and the combinations of repeats in various type of consensus sequences derived from the proteins of the major ampullate gland dragline silk and/or proteins of the minor ampullate gland, and/or Flag proteins of the orb weaving spider net silk, in particular, selectable from the group including the consensus sequences:

```
                                           (SEQ ID NO: 23)
MaSp1
GGAGQGGYGRGGAGQGGAGAAAAAAAA (SEQ ID NO: 24)
MaSp2
GGAGPGRQQGYGPGSSGAAAAAAA (SEQ ID NO: 25)
MiSp1
GAGAGAGAAAGAGAGAGGAGYGGQGGYGAGAGAGAAAAAGAGAGGAGGY
GR (SEQ ID NO: 26)
MiSp2
GAGVGAGAAAGFAAGAGGAGGYR

Flag
ISEELTIGGAGAGGVGPGGSGPGGVGPGGSGPGGVGPGGSGPGGVGSGG
SGPGGVGPGGS

GPGGVGSGGFGPGGIGPGGSGPGGVGPGGVGGPYGPGGSGPGGAGGAGG
SYGPGGPYGPG

GSGGPGGAGGPYGPGGAGGPYGPGGPYGPGGAGGPGGEGPGGAGGPYGP
GGPGGAGPGGY

GPGGAGPGGYGPGGAGPGGYGPGGAGSGGYGPGGAGPGGYGPGGPGPGG
YGPGGAGPGGY

GPGGTGPGGSAPGGAGPGGAGPGGYGPGGSGPGGYGPGGGPGGAGPGGA
GPGGAGPGGAG

PGGAGPGGAGPGGAGPGGAGPGGAGPGGAGPGGVGTGGLGRGGAGRGGA
GRGGAGRGGAG (SEQ ID NO: 27)
RGGAGRGGTGGVGGAGGAGGAGGVGGAGGSGGTTVIEDLDITIDGADGP
IT,
``` wherein:

MaSp1 and MaSp1 are the proteins of the *Latrodectus hesperus* major ampullate gland dragline silk [Lawrence B. A. et al., 2004, Biomacromolecules, v. 5, 689-695];

MiSp1 and MiSp1 are the proteins of the *Nephila clavipes* minor ampullate gland [Colgin M. A. & Lewis R. V., 1998, Protein Sci., v. 7, 667-672];

Flag is the *Nephila madagascariensis* net silk protein [Hayashi C. & Lewis R. V., 1998, J. Mol. Biol., v. 275, 773-784].

According to the inventive method, consensus sequences are used preferably derived from the repetitive sequences of the proteins of the *Nephila clavipes* and *Nephila madagascariensis* major ampullate gland and selectable from the group of:

```
                                                  (SEQ ID NO: 9)
AGQGGYGGLGSQGAGRGGLGGQGAGAAAAAAGGAGQGGLGGQG (SEQ ID NO: 10)
AGQGAGASAAAAGGAGQGGYGGLGSQG (SEQ ID NO: 11)
AGRGGLGGQGAGAVAAAAAGGAGQGGYGGLGSQG (SEQ ID NO: 12)
AGRGGQGAGAAAAAAGGAGQRGYGGLGNQG (SEQ ID NO: 13)
GPGGYGPGQQGPGAAAAASA (SEQ ID NO: 14)
GRGPGGYGPGQQGPGGSGAAAAAA (SEQ ID NO: 15)
GSGPGGYGPGQQGPGGPGAAAAAAA (SEQ ID NO: 16)
GRGPGGYGPGQQGPGQQGPGGSGAAAAAA (SEQ ID NO: 17)
GRGPGGYGPGQQGPGGPGAAAAAA (SEQ ID NO: 18)
GPGGYGPGQQGPGAAAAAAA (SEQ ID NO: 19)
GSGAGGYGPGQQGPGGPGAAAAAA (SEQ ID NO: 20)
GSGPGGYGPGQQGPGGSAAAAAA (SEQ ID NO: 21)
GSGPGGYGPGQQGPGGSGAAAAAAAA (SEQ ID NO: 22)
GRGPGGYGQGQQGPGGPGAAAAAA.
```

Construction of artificial genes encoding the recombinant proteins of the major and/or minor ampullate glands or Flag proteins of the orb weaving spider net silk comprises reconstructing the DNA sequence encoding the consensus sequence or combinations of repeats of various types of consensus sequences derived from the repetitive sequences of the above proteins; constructing and chemically synthesizing a series of primers for the consensus sequence/sequences; simultaneously annealing a mixture of all synthesized primers necessary to form a two-stranded DNA molecule, and subsequently treating thereof with ligase to remove single-stranded DNA breaks, or causing a polymerase chain reaction to occur successively using the required primers and completing step-by-step the rising DNA fragment, wherein the fragment being formed ("monomer") then undergoes a step-by-step duplication within the plasmid until a required gene length is obtained [Bogush V. G. at al., 2001, Biotechnologies, v. 2, 11-22; Bogush V. G. at al., 2006, Biotechnologies, т. 4, 3-12; Bogush V. G. & Debabov V. G., 2009, J. Neuroimmune Pharmacol., v. 4, 17-27].

The sequences of the respective cDNAs may be derived based on the sequences of a natural protein subject to the degeneracy of code and frequency of occurrence of codons in the yeast. In particular, when constructing the gene encoding the 1F9 protein and comprising 9 "monomer" copies, the fragments encoding the most typical primary repeats have been selected form the natural protein sequences and differed from each other in the set of deletions. The reconstructed DNA sequence included approximately 400,000 nucleotide pairs, encoding the polypeptide corresponding to 134 amino acid residues. "Rare" codons in the artificial gene sequence have been replaced with the most often used ones in the yeast. A "monomer" has been obtained by the chemical-fermentative synthesis, and a multimeric form has been obtained by a step-by-step multiplication of the monomer within the recombinant plasmid [Bogush V. G. at al., 2001, Biotechnologies, v. 2, 11-22].

When constructing the 2E12 gene, type 2 spidroin sequences of the major ampullate gland have been used, available in the database of the NCBI protein sequences and comprising more than 200 amino acid residues. Based on the mathematical analysis of all sequences, block sequences have been developed (each consisting of 3-5 primary repeats) and a formula of compete artificial gene has been drafted [Bogush V. G. et al., 2009, J. Neuroimmune Pharmacol., v. 4, 17-27].

In a preferred embodiment, the proposed method for producing a recombinant protein of the orb weaving spider silk in the yeast cells comprises fusing the spider silk recombinant protein gene with a DNA sequence encoding ubiquitin or *Saccharomyces cerevisiae* SUMO protein.

In one of the most preferred embodiments of the invention, the recombinant 1F9 protein of the *Nephila clavipes* orb weaving spider dragline silk is obtained in the cells of *Saccharomyces cerevisiae*, wherein the 1F9 structural gene is fused with the DNA sequence encoding *Saccharomyces cerevisiae* ubiquitin. In still other most preferable embodiment of the invention, the recombinant 2E12 protein of *Nephila madagascariensis* orb weaving spider dragline silk is obtained in the cells of *Saccharomyces cerevisiae*, wherein the 2E12 gen is fused with the DNA sequence encoding *Saccharomyces cerevisiae* ubiquitin.

In still other most preferable embodiment of the invention, a fused protein comprising a sequence of the recombinant 1F9 protein is expressed in the *Saccharomyces cerevisiae* yeast cells, wherein the 1F9 sequence is fused with the sequence of *Saccharomyces cerevisiae* SUMO protein. The recombinant proteins obtainable according to the inventive method have been isolated from the water insoluble fractions of the *Saccharomyces cerevisiae* host cells by chromatography on a cation-exchange column (Examples 9 and 11). The electrophoretic analysis of the fractions (FIGS. 1 and 2) has shown that the recombinant 1F9 and 2E12 proteins are accumulated in the water insoluble protein fractions of the yeast cells (recombinant proteins are essentially absent in the water soluble fractions) and are free of the ubiquitin-like protein component. This is demonstrated by the electrophoretic mobility of the analyzed proteins and the absence of bands in the gel whose mobility corresponds to that of the fused proteins (ubiquitin-1F9 and ubiquitin-2E12). Similar results have been obtained for the recombinant proteins isolated and purified from the water insoluble fractions of the *Saccharomyces cerevisiae* host cells producing the spider silk recombinant proteins fused with the SUMO protein. The production of the recombinant proteins by the *Saccharomyces cerevisiae* cells is at least 100 mg/l of the fermentative culture.

The absence of the recombinant proteins obtained in accordance with the invention in the water soluble fraction makes it possible essentially to avoid the loss of protein in the process of isolation and purification in contrast to the prior art method [Bogush V. G. at al., 2001, Biotechnologies, т. 2, 11-22] wherein only about 80% of the target protein was found in the water insoluble fraction.

Therefore, when obtaining the spider silk recombinant protein by the method according to the invention, the recombinant protein synthesized in the *Saccharomyces cerevisiae* cells is accumulated in the water insoluble protein fractions in the form of a processed protein free of the hybrid component, wherein the cells expressing the spider silk recombinant protein accumulate tens times more recombinant protein than according to the prior art methods.

The purified recombinant proteins of the orb weaving spider silk according to the invention are able to form various types of supramolecular structures, in particular the analyzed proteins form the water insoluble threads (Example 12, FIG. 8).

In another aspect, the invention provides fused proteins comprising the sequences of the orb weaving spider silk recombinant protein and of ubiquitin-like protein occupying an N-terminal position with respect to the spider silk recombinant protein within the fused protein, wherein the sequence of the spider silk recombinant protein comprises consensus sequences derived from repetitive sequences of the MaSp1 and MaSp2 proteins of the major ampullate gland, MiSp1 and MiSp2 proteins of the minor ampullate gland, and Flag protein of the orb weaving spider net silk.

In a preferred embodiment, the invention provides a fused protein wherein a ubiquitin-like protein comprises ubiquitin or *Saccharomyces cerevisiae* SUMO protein, and the sequence of the orb weaving spider silk recombinant protein comprises consensus sequences derived from repetitive sequences of MaSp1 and MaSp2 proteins of the *Nephila clavipes* and *Nephila madagascariensis* major ampullate gland and selectable from the group of:

```
                                              (SEQ ID NO: 9)
AGQGGYGGLGSQGAGRGGLGGQGAGAAAAAAAGGAGQGGLGGQG (SEQ ID NO: 10)
AGQGAGASAAAAGGAGQGGYGGLGSQG (SEQ ID NO: 11)
AGRGGLGGQGAGAVAAAAAGGAGQGGYGGLGSQG (SEQ ID NO: 12)
AGRGGQGAGAAAAAAGGAGQRGYGGLGNQG (SEQ ID NO: 13)
GPGGYGPGQQGPGAAAAASA (SEQ ID NO: 14)
GRGPGGYGPGQQGPGGSAAAAAA (SEQ ID NO: 15)
GSGPGGYGPGQQGPGGPAAAAAAA (SEQ ID NO: 16)
GRGPGGYGPGQQGPGQQGPGGSAAAAAA (SEQ ID NO: 17)
GRGPGGYGPGQQGPGGPAAAAAA (SEQ ID NO: 18)
GPGGYGPGQQGPGAAAAAAA (SEQ ID NO: 19)
GSGAGGYGPGQQGPGGPAAAAAA (SEQ ID NO: 20)
GSGPGGYGPGQQGPGGSSAAAAAA (SEQ ID NO: 21)
GSGPGGYGPGQQGPGGSGAAAAAAAA (SEQ ID NO: 22)
GRGPGGYGQGQQGPGGPGAAAAAA.
```

Most preferably, the fused protein comprises a sequence of the recombinant 1F9 protein of the *Nephila clavipes* orb weaving spider dragline silk, fused with a sequence encoding ubiquitin or *Saccharomyces cerevisiae* SUMO protein as shown in the Listing of Sequences (SEQ ID NO:1 and SEQ ID NO:3, respectively).

In another most preferred embodiment, the fused protein comprises a sequence of the recombinant 2E12 protein of the *Nephila madagascariensis* orb weaving spider dragline silk, fused with a sequence encoding ubiquitin or *Saccharomyces cerevisiae* SUMO protein.

In still another aspect, the invention provides recombinant DNAs encoding fused proteins. The synthesized and cloned DNA sequences used according to the invention for obtaining the spider silk recombinant proteins, encode the fused proteins comprising the sequences of the orb weaving spider silk recombinant protein and ubiquitin-like protein occupying an N-terminal position within the fused protein with respect to the recombinant protein, wherein the sequence of the spider silk recombinant protein comprised consensus sequences derived from repetitive sequences of the MaSp1 and MaSp2 proteins of the major ampullate gland, MiSp1 and MiSp2 proteins of the minor ampullate gland and Flag protein of the orb weaving spider net silk.

Preferably, the recombinant DNA encodes the fused protein wherein the ubiquitin-like protein comprises ubiquitin or *Saccharomyces cerevisiae* SUMO protein, and the sequence of the orb weaving spider silk recombinant protein comprises consensus sequences derived from repetitive sequences of the MaSp1 and MaSp2 proteins of the *Nephila clavipes* and *Nephila madagascariensis* major ampullate gland and selectable from the group of:

```
                                              (SEQ ID NO: 9)
AGQGGYGGLGSQGAGRGGLGGQGAGAAAAAAAGGAGQGGLGGQG (SEQ ID NO: 10)
AGQGAGASAAAAGGAGQGGYGGLGSQG (SEQ ID NO: 11)
AGRGGLGGQGAGAVAAAAAGGAGQGGYGGLGSQG (SEQ ID NO: 12)
AGRGGQGAGAAAAAAGGAGQRGYGGLGNQG (SEQ ID NO: 13)
GPGGYGPGQQGPGAAAAASA (SEQ ID NO: 14)
GRGPGGYGPGQQGPGGSAAAAAA (SEQ ID NO: 15)
GSGPGGYGPGQQGPGGPAAAAAAA (SEQ ID NO: 16)
GRGPGGYGPGQQGPGQQGPGGSAAAAAA (SEQ ID NO: 17)
GRGPGGYGPGQQGPGGPAAAAAA
```

-continued

GPGGYGPGQQGPGAAAAAAA (SEQ ID NO: 18)

GSGAGGYGPGQQGPGGPGAAAAAA (SEQ ID NO: 19)

GSGPGGYGPGQQGPGGSSAAAAAA (SEQ ID NO: 20)

GSGPGGYGPGQQGPGGSGAAAAAAA (SEQ ID NO: 21)

GRGPGGYGQGQQGPGGPGAAAAAA. (SEQ ID NO: 22)

Most preferably, the recombinant DNAs used according to the invention for obtaining the spider silk recombinant proteins encode the recombinant 1F9 protein of the *Nephila clavipes* orb weaving spider dragline silk or the recombinant 2E12 protein of the *Nephila madagascariensis* orb weaving spider dragline silk whose sequences are fused with the sequence encoding ubiquitin or *Saccharomyces cerevisiae* SUMO protein as shown in the Listing of Sequences (SEQ ID NO:1, SEQ ID NO:2 and SEQ ID NO:3). The DNAs according to the present invention further comprise the encoding sequences subject to the degeneracy of code and the sequences used as primers in the amplification reactions.

The proteins according to the invention are obtained in the yeast cells using the expression vectors consisting of a gen of the fused protein comprising the sequences of the orb weaving spider silk recombinant protein and of the ubiquitin-like protein, and high efficient controllable yeast promotors, in particular such as GAL1, GPD1, CUP1. As the suitable vectors for constructing the expression vectors according to the invention, episomal vectors may be used comprising a replication initiation point of the endogenic 2-µm yeast plasmid whereby their ability is ensured to be maintained in the eposomal amplifying state in the yeast cells.

In a preferred embodiment of the invention, expression vectors are constructed to carry the recombinant DNA encoding the fused protein wherein the ubiquitin-like protein comprises ubiquitin or *Saccharomyces cerevisiae* SUMO protein, and the sequence of the orb weaving spider silk recombinant protein comprises consensus sequences derived from repetitive sequences of the MaSp1 and MaSp2 proteins of the *Nephila clavipes* and *Nephila madagascariensis* major ampullate gland.

Figure 3:
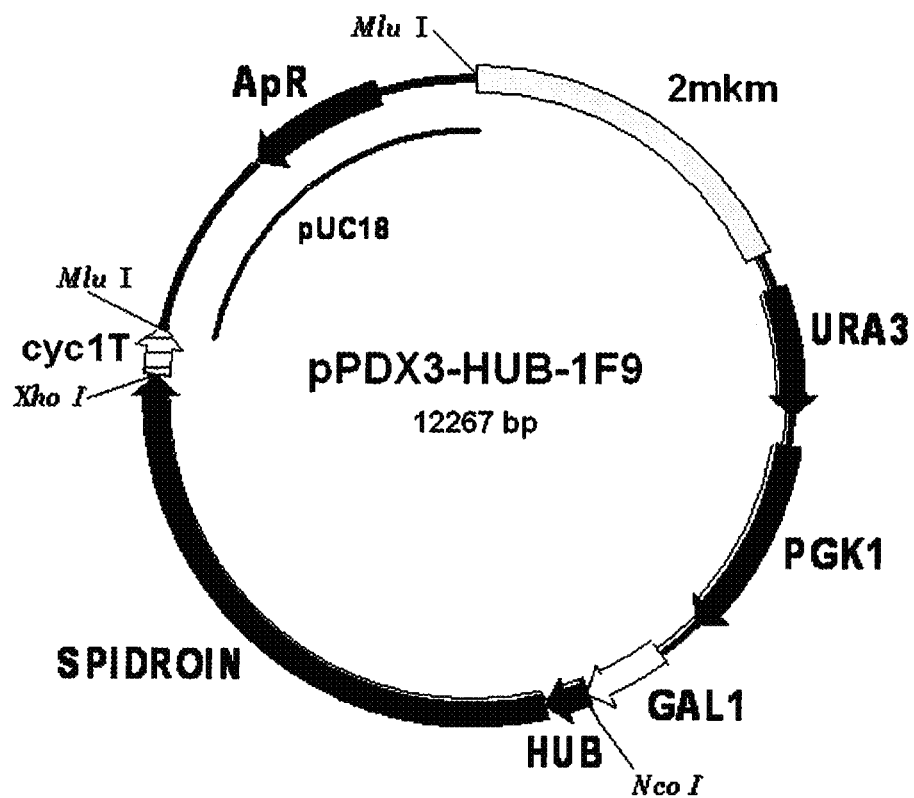
FIG. 3 shows a map of pPDX3-HUB-1F9 vector. Legend: SPIDROIN—synthetic gene of recombinant 1F9 protein (*N. clavipes* spider spidroin-1); HUB—gene of *S. cerevisiae* ubiquitin; GAL1—GAL1 gene promotor region of *S. cerevisiae* yeast; URA3 and PGK1—structural URA3 and PGK1 genes of *S. cerevisiae* yeast, respectively; cyc1T—sequence of CYC1 gene transcription terminator of *S. cerevisiae* yeast; 2 mkm—fragment of endogenous 2-µm plasmid of *S. cerevisiae* yeast, comprising a replication initiation point; pUC18—fragment of pUC18 plasmid, comprising a beta-lactamase (ApR) gen and a replication initiation point to enable selective vector amplification in the cells of *E. coli*.
Figure 5:
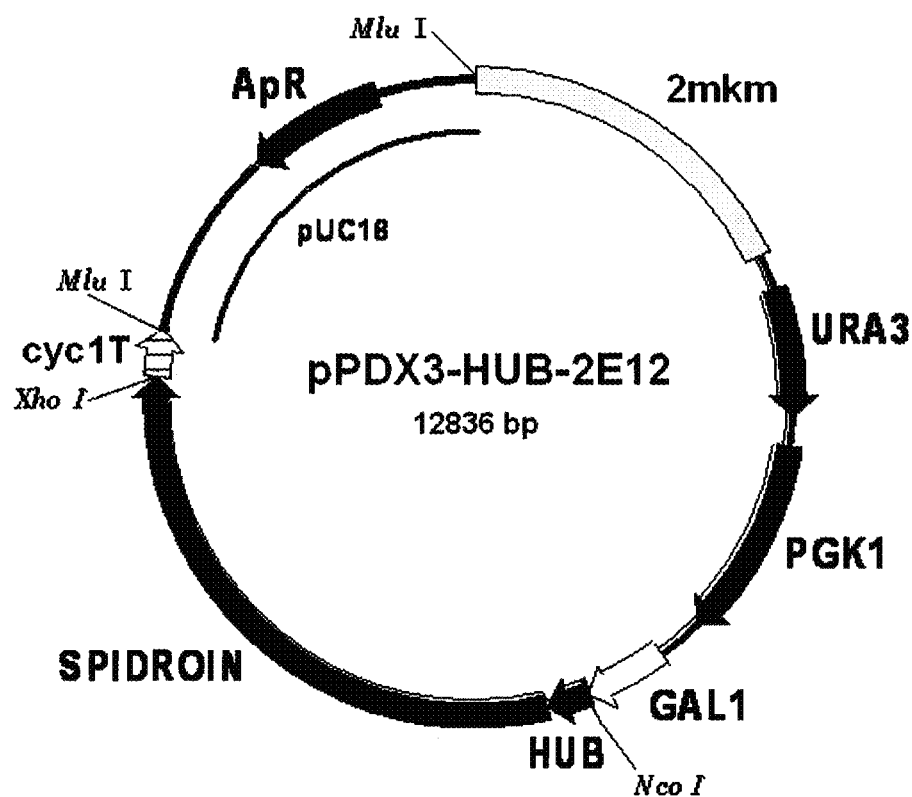
FIG. 5 shows a chart of pPDX3-HUB-2E12 vector. Legend: SPIDROIN—DNA sequence encoding recombinant 2E12 protein; HUB—DNA sequence encoding *S. cerevisiae* yeast ubiquitin; GAL1—GAL1 gene promotor region of *S. cerevisiae* yeast; URA3 and PGK1 structural URA3 and PGK1 genes of *S. cerevisiae* yeast, respectively; cyc1T—sequence of CYC1 gene transcription terminator of *S. cerevisiae* yeast; 2 mkm—fragment of endogenic 2-µm plasmid of *S. cerevisiae* yeast, comprising a replication initiation point; pUC18—fragment of pUC18 plasmid, comprising a beta-lactamase (ApR) gene and a replication initiation point to enable selective vector amplification in the cells of *E. coli*.
Figure 6:
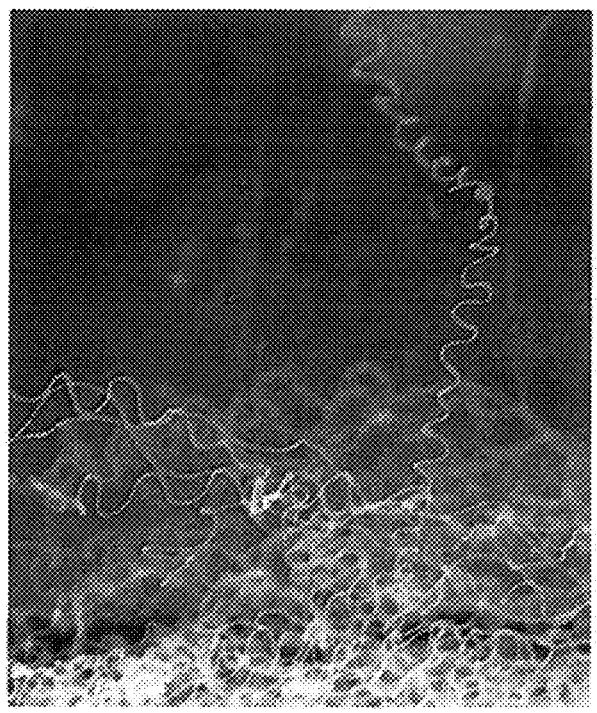
FIG. 6 shows a photograph of an artificial thread from 1F9 protein in a vessel with ethanol.

In one of the most preferred embodiments of the invention, pPDX-HUB-1F9 (FIG. 3) and pPDX3-HUB-2E12 (FIG. 5) expression bireplicon vector are constructed, which are obtained by cloning the sequences of the 1F9 or 2E12 structural genes, respectively, in the pPDX3-HUB plasmid carrying as part thereof, under control of the GAL1 yeast promotor region, *Saccharomyces cerevisiae* ubiquitin gen, wherein the sequences of the 1F9 or 2E12 structural gene and ubiquitin gen are fused in each case within a single reading frame.

Figure 4:
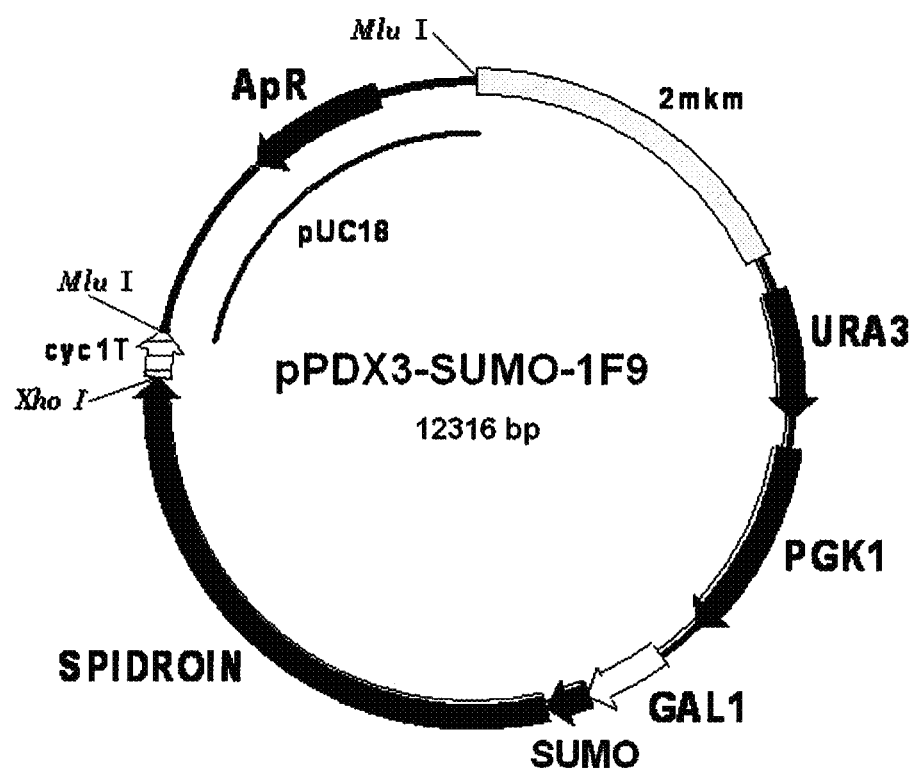
FIG. 4 shows a map of pPDX3-SUMO-1F9 vector. Legend: SPIDROIN—synthetic gene of recombinant 1F9 protein (*N. clavipes* spider spidroin-1); SUMO—SMT3 gen of *S. cerevisiae* yeast, encoding SUMO protein; GAL1—GAL1 gene promotor region of *S. cerevisiae* yeast; URA3 and PGK1—structural URA3 and PGK1 genes of *S. cerevisiae* yeast, respectively; cyc1T—sequence of CYC1 gene transcription terminator of *S. cerevisiae* yeast; 2 mkm—fragment of endogenic 2-nm plasmid of *S. cerevisiae* yeast, comprising a replication initiation point of yeast; pUC18—fragment of pUC18 plasmid, comprising a beta-lactamase (ApR) gene and a replication initiation point to enable selective vector amplification in the cells of *E. coli*.

In still another most preferred embodiments of the invention, pPDX3-SUMO-1F9 expression bireplicon vector is constructed, which is obtained by cloning the sequences of the 1F9 protein gene pPDX3-SUMO plasmid carrying as part thereof, under control of the GAL1 yeast promotor region, the SMT3 structural gene of *Saccharomyces cerevisiae* encoding *Saccharomyces cerevisiae* SUMO protein, wherein cloning results in fusing the sequences 1F9 and SMT3 genes within a single reading frame (FIG. 4). The pPDX3-HUB-1F9, pPDX3-HUB-2E12 and pPDX3-SUMO-1F9 expression vectors comprise a replication initiation point of endogenic 2-µm yeast plasmid whereby their ability is ensured to be maintained in the eposomal amplifying state in *Saccharomyces cerevisiae* yeast cells.

In accordance with an aspect, the invention provides yeast host cells producing the recombinant proteins of the orb weaving spider silk. As the host cells suitable for obtaining the spider silk recombinant proteins, yeast cells are use selected from the group including *Saccharomyces cerevisiae, Kluyveromyces lactis, Hansenula polymorpha, Pichia pastoris* and *Schizosaccharomyces pombe*. Preferred host cells are the *Saccharomyces cerevisisae* cells. Most preferably, as the host cells, *Saccharomyces cerevisiae* D702 diploid recipient strain is used so that an enhanced stability of its expression characteristics is enabled. *Saccharomyces cerevisiae* D702 comprises homozygous mutations in the chromosome alleles of structural PGK1 gene encoding phosphoglycerate kinase so that a stable maintenance of the vector is enabled in the media containing any single carbon source assimilable by *Saccharomyces cerevisiae*, and of the GAL80 gene encoding the GAL1 promotor repressor protein, and also a homozygous mutation leading to a change in the regulation of the GAL4 gene encoding the GAL1 promotor activator protein whereby the galactose-controllable expression of the genes being under control of the GAL1 promotor takes place.

In one of the most preferred embodiments of the invention, the cells of *Saccharomyces cerevisiae* D702 recipient strain are transformed by means of the pPDX3-HUB-1F9 expression vector. The resulting SCR-702-1F9 strain producing the recombinant 1F9 protein of the *Nephila clavipes* orb weaving spider silk dragline silk is deposited at the Russian National Collection of Industrial Microorganisms (VKPM) as *Saccharomyces cerevisiae* VKPM Y-3583 strain.

In a still other most preferred embodiment of the invention, the cells of the *Saccharomyces cerevisiae* D702 recipient strain are transformed by means of the pPDX3-HUB-2E12 expression vector. The resulting SCR-702-2E12 strain producing the recombinant 2E12 protein of the *Nephila madagascariensis* orb weaving spider silk dragline silk is deposited at the Russian National Collection of Industrial Microorganisms (VKPM) as *Saccharomyces cerevisiae* VKPM Y-3584 strain.

In a yet still other most preferred embodiment of the invention, the cells of the *Saccharomyces cerevisiae* D702 recipient strain are transformed by means of the pPDX3-SUMO-1F9 expression vector.

Characteristics of the Producer Strains

Genotype:

SCR-702-1f9 (a/α leu2/leu2 ura3/ura3 trp1/trp1 gal80::LEU2/gal80::LEU2 lys7/LYS7 his3/HIS3 his4/HIS4 pgk1:URA3/pgk1:URA3 GAL4:(STA2p-GAL4,TRP1)/GAL4:(STA2p-GAL4, TRP1) STA2/STA2 suc⁰/SUC2)/pPDX3-1f9

SCR-702-2E12 (a/α leu2/leu2 ura3/ura3 trp1/trp1 gal80:LEU2Igal80:LEU2 lys7/LYS7 his3/HIS3 his4/HIS4 pgk1:URA3/pgk1:URA3 GAL4:(STA2p-GAL4,TRP1)/GAL4:(STA2p-GAL4, TRP1) STA2/STA2 suc⁰/SUC2)/pPDX3-2E12

Morphological Characters

When cultivated at 28° C. for 48 hours on the YPD agar medium formulated as follows (in wt. %): peptone—2, yeast extract—1, glucose—2, agar—2, water—balance, the cells of *Saccharomyces cerevisiae* producer strains have an oval shape of 3-7 µm in diameter. The cells reproduced by budding. The budding is true, multisite. No true mycelium is formed. The colonies have the following appearance:

1) on the YPD agar medium—white color colonies with an even edge, mat surface, lenticular profile and creamy texture;

2) on the agar medium with starch formulated as follows (in wt. %): peptone—2, yeast extract—1, starch—1, agar—2, water—balance)—white color colonies with an figured edge, mat surface, lenticular profile and grainy texture.

Cultivation in a liquid medium with starch: for the first 24 hours of cultivation at 28° C.—a cloudy liquid with a white precipitate without caking and forming no near-wall films.

Physicochemical Features

The two strains are facultative anaerobes. Growth temperature: at 20-33° C. (optimum, at 28° C.). Cultivation pH: 3.8-7.4 (optimum, 5.0).

Assimilation of Carbon Sources

The two strains cause fermentation of glucose, fructose, maltose, sucrose, dextrins, starch, and cause no fermentation of lactose, galactose, inulin, xylose, arabinose.

Assimilation of Nitrogen Sources

The two strains assimilate amino acids, ammonium sulfate, ammonium nitrate.

Storage

The strains are stored at −70° C. in a 20% aqueous solution of glycerin. Storage on an agar rich medium with glucose is possible for 3 months at +4° C.

Stability

The claimed strains remain stable during 20 consecutive passages on the YPD agar medium at 28° C.

Pathogenicity

The strains are nonpathogenic.

The invention will be illustrated by the following examples provided for the purposes of demonstration rather than limitation of the scope of claims.

EXAMPLES

Example 1

Construction of the pPDX3-HUB Vector

A structural gene of the yeast ubiquitin was amplified in a polymerase chain reaction using as a matrix a chromosomal DNA of the *S. cerevisiae* Y618 laboratory strain [Kartasheva et al., 1996, Yeast, v. 12, 1297-13] isolated by the method according to Sidoruk [Sidoruk et. al., 2008, "Actual problems of genetics, radiobiology and radioecology", Collected theses and reports, Dubna, JINR, p. 100]. N513 (5'-ataccatggaacatcatcatcatcatggaggcatgcagatct-tcgtcaagactttga (SEQ ID NO: 28)) and N514 (5'-actggatc-cacctcttagccttagcacaac (SEQ ID NO: 29)) were used as amplification primers. The amplified DNA fragment of 510 base pairs was eluted from the agarose gel using the Qiagen kit (Qiagen, Cat. No 28706), treated with NcoI and BamHI restrictases, and cloned in the pUC18x-GAL1-NcoI laboratory plasmid cleaved at the same sites and carrying the HindIII/NcoI DNA fragment encoding the GAL1 gene promotor region of *S. cerevisiae* yeast. As a result, the p101-25 plasmid was obtained comprising a nucleotide sequence encoding *S. cerevisiae* yeast ubiquitin and fused with the nucleotide sequence of the GAL1 gene promotor region of *S. cerevisiae* yeast. The p101-25 plasmid comprises the XhoI restrictase recognition site in the polylinker region following the BamHI cloning site.

The HindIII/XhoI DNA fragment of the p101-25 plasmid, comprising the GAL1 gene promotor region and the nucleotide sequence encoding ubiquitin was cloned in the pPDX3 laboratory vector whose DNA was cleaved at the same sites. As a result of cloning, the pPDX3-HUB vector was obtained that was used to clone the genes of the spider silk recombinant proteins.

Example 2

Construction of the pPDX3-HUB-1F9 Expression Vector

The pPDX3-HUB-1F9 expression vector (FIG. 3) was obtained as a result of cloning the BglII/XhoI DNA fragment of the pUC21-1F9 laboratory plasmid of 36,000 nucleotide pairs, comprising the gen of 1F9 protein, in the pPDX3-HUB vector whose DNA was cleaved at the sites of BamHI and XhoI. As a result of cloning, the pPDX3-HUB-1F9 expression vector was obtained wherein the structural gene of 1F9 was fused with the ubiquitin-encoding structural gene within a single reading frame. The vector was used for expression of 1F9 in *S. cerevisiae* yeast cells.

Example 3

Construction of the pPDX3-HUB-2E12 Vector

The pPDX3-HUB-2E12 expression vector was obtained as a result of cloning the BglII/XhoI DNA fragment of the laboratory plasmid pUC21-2E12 of 42,000 nucleotide pairs, comprising the gen of 2E12 protein, in the pPDX3-HUB vector whose DNA was cleaved at the sites of BamHI and XhoI. As a result of cloning the pPDX3-HUB-2E12 expression vector was obtained wherein the structural gene of 2E12 was fused with the ubiquitin-encoding structural gene within a single reading frame. The vector was used for expression of 2E12 in *S. cerevisiae* yeast cells.

Example 4

Construction of the pPDX3-SUMO Vector

The structural SMT3 gene of *S. cerevisiae* yeast encoding SUMO protein was amplified in a polymerase chain reaction using as a matrix a chromosomal DNA of the *S. cerevisiae* laboratory strain as in Example 1. Two-stage amplification was carried out. First, the two overlapping DNA fragments were amplified using the following primer pairs:

```
                                           (SEQ ID NO: 30)
Fragment 1 of 129 base pairs:
N450
(5'-atatccatggaaaagagatctgactcagaagtcaatcaagaa)

(SEQ ID NO: 31)
N454
(5'-cttgaagaaaatctctgaa)

(SEQ ID NO: 32)
Fragment 2 of 230 base pairs:
N453
(5'-ttcagagatttttcttcaag)

(SEQ ID NO: 33)
N452
(5'-atatcaattggatccaccaatctgttctctgtga).
```

The amplified DNA fragments were eluted from the agarose gel and used for PCR-ligation. To this end, the mixture of fragments 1 and 2 was used as a PCR matrix with N450 and N452 used as primers. The DNA fragment of 290 base pairs resulting from the PCR was eluted from the agarose gel, treated with BglII and BamHI restrictases, and cloned into the BamHI site of the pUC18x-GAL1-BamHI laboratory plasmid carrying the HindIII/BamHI DNA fragment encoding the GAL1 gene promotor region of *S. cerevisiae* yeast comprising the ATG codon and the BamHI site (underlined) in the ATGCATGGATCC sequence (SEQ ID NO: 34). As a result, the sequences of SMT3 gene of *S. cerevisiae* yeast were fused with the sequences encoding the GAL1 gene promotor region of *S. cerevisiae* yeast. Finally, the p101-18 plasmid was obtained wherein the cloned SMT3 gen was sequenced.

The resulting p101-18 plasmid contains a DNA fragment wherein the SMT3 gen of the yeast is fused with the GAL1 gene yeast promotor region. In the polylinker region of the p101-18 plasmid following the BamHI cloning site, the restrictase XhoI recognition site is located.

The HindIII/XhoI DNA fragment of the p101-18 plasmid, including the GAL1 gene promotor region and the cloned SMT3 gene was cloned into the pPDX3 laboratory vector whose DNA is cleaved at the same sites. As a result of cloning, the pPDX3-SUMO vector was obtained that was used for cloning the genes of the spider silk recombinant proteins.

Example 5

Construction of the pPDX3-SUMO-1F9 Vector

The pPDX3-SUMO-1F9 expression vector (FIG. 4) was obtained as a result of cloning the BglII/XhoI DNA fragment of the pUC21-1F9 laboratory plasmid of 36,000 nucleotide pairs, comprising the gen of 1F9 protein, in the pPDX3-SUMO vector, whose DNA was cleaved at the sites of BamHI and XhoI. As a result of cloning the pPDX3-HUB-1F9 expression vector was obtained, wherein the structural gene of 1F9 was fused with the ubiquitin-encoding structural gene within a single reading frame. The vector was used for expression of 1F9 in *S. cerevisiae* yeast cells.

Example 6

Construction of the SCR-702-1F9 Producer Strain of 1F9 Protein (VKPM Y-3583)

The SCR-702-1F9 strain was obtained by transformation of the D702 laboratory strain with the pPDX3-HUB-1F9 expression vector. For performing the transformation, the D702 cells were grown for 18-24 hours at 28° C. on the YPGE agar medium formulated as follows (in wt. %): bactopeptone—2, yeast extract—1, bactoagar—2, ethanol—2, glycerol—3, water—balance. The cultivated D702 cells were transformed by the method according to Ito et. al. [Ito et al., 1983, J. Bacteriol., v. 153, 163-168]. Transformants were selected according to their ability to grow on the YPD medium formulated as follows (in wt. %): bactopeptone—2, yeast extract—1, glucose—2, bactoagar—2, water—balance. One of the resulting transformants is referred to as SCR-702-1F9.

Example 7

Construction of the SCR-702-2E12 Producer Strain of 2E12 Protein

The SCR-702-2E12 strain was obtained by transformation of the D702 laboratory strain pPDX3-HUB-2E12 expression vector. Transformation was performed as in Example 6. The SCR-702-2E12 strain is deposited at the Russian National Collection of Industrial Microorganisms as *Saccharomyces cerevisiae* VKPM Y-3584 strain.

Example 8

Construction of the D702-SUMO-1F9 Producer Strain of the 1F9 Protein

The D702-SUMO-1F9 strain was obtained by transformation of the D702 laboratory strain with the pPDX3-SUMO-1F9 expression vector. Transformation was performed as in Example 4 except for the use of the pPDX3-SUMO-1F9 plasmid.

Example 9

Analysis of the Expression of 1F9 and Recombinant 2E12 Proteins in the Cells of *Saccharomyces cerevisiae* Strains The cells of *S. cerevisiae* VKPM Y-3583, VKPM Y-3584 or D702-SUMO-1F9 were cultivated in the flasks at 30° C. in a rotary shaker at a speed of 250 rpm on the liquid YPD medium formulated as follows (in wt. %): bactopeptone—2, yeast extract—1, glucose—2, water—balance, with the population of $5\times10^5$-$5\times10^6$ ml$^{-1}$ plated per titer. Assays were taken after 46 hours of cultivation. The final optical density of the culture was $OD_{600}$=40-45. The cells were separated from the culture medium by settling in a centrifuge at 10,000 g for 1 minute and used for further analysis for expression of 1F9 and 2E12 proteins by microtechnique in a 1.5-ml vial. To this end, the cell precipitate was suspended in a "breakdown buffer" (0.05 M sodium phosphate, 2.5 mM EDTA, 5% glycerol) on the basis of 100 µl of the buffer per 100 µl humid cell precipitate. Cell breakdown is accomplished using glass beads (d=0.45-0.65 mm) on a Vortex type vial shaker. To this end, 570 mg of beads was mixed with 200 µl of the cell suspension, the mixture was shaken at 0° C. for 90 seconds, 250 µl of the "breakdown buffer" was added to the vials and shaking was repeated for 60 more. 500 µl of the "breakdown buffer" was added to the vials, the content was mixed together and then the resulting samples were centrifuged for 10 minutes at 16000 g. The pH of the supernatant containing water soluble proteins of the yeast cells was adjusted to 4.0 with 1M of a sodium acetate solution, and the precipitate was removed by centrifugation for 5 minutes at 16,000 rpm; then the supernatant was heated at 65° C. for 20 minutes and the precipitated ballast proteins were removed by centrifugation; the resulting solution was subjected to dialysis for 40 minutes against 10 mM of sodium acetate, pH 4.0. The precipitated water insoluble proteins were suspended in 750 µl of the "breakdown buffer", transferred to the new vials and centrifuged for 15 minutes at 16000 g. The resulting precipitate (100 µl) containing the target proteins was suspended in 400 µl of the "6.5 G" buffer (6.5 M guanidine hydrochloride or guanidine thiocyanate solution in a containing 0.1 M sodium phosphate, 0.01 M Tris-HCl, pH 6.5), the target proteins were extracted overnight on a magnetic stirrer at +4° C. Then, the suspension was centrifuged for 15 minutes at 16000 g, the supernatant together with the target protein having moved thereto was subjected to dialysis against 300 ml of 5 mM sodium acetate for 1.5 hour. The resulting sample was centrifuged for 15 minutes at 16000 g, and the supernatant was used to perform the electrophoretic analysis for the level of target protein production.

Figure 2:
FIG. 2 shows electrophoresis in 12% polyacrylamide gel with DDS-Na of 2E12 fractions after chromatography in the HiPrep 16/10 SP FF cation-exchange column; tracks: 1—original solution before application onto the column; 2—breakthrough fraction; 3—standards of molecular weights (from top downward, in kDa): 170, 130, 95, 72, 55, 43, 34, 26, 17; 4—fraction containing 2E12; 5—standard 2E12 sample.

The electrophoretic analysis for target protein was performed using 12% PAAG-DDS-Na according to the standard Laemmli procedure [Laemmli, 1970, Nature, v. 227, 680-685]. To this end, the solution was diluted approximately в 500-1000 times with "sample buffer" (0.0625 M Tris-HCl, pH 6.8, 2 wt. % DDS-Na, 0.0025 wt. % bromophenol blue), and boiled in a water bath for 5 minutes. Aliquots of 3-15 μl were applied onto the 12% PAAG and subjected to electrophoresis in the Bio Rad MiniPROTEAN apparatus until the dye frontline is at 1 cm from the gel end. The gels were washed in the water and dyed in a 0.2% solution of Coomassie R-250 (Fermentas). The electrophoretic analysis showed that 1F9 and 2E12 proteins are accumulated in the water insoluble fraction of the S. cerevisiae yeast cell protein and are free of the SUMO component or ubiquitin (FIGS. 1 and 2). This is demonstrated by the electrophoretic mobility of the analyzed proteins and the absence of protein bands in the gel whose mobility corresponds to that of the hybrid 1F9 and 2E12 proteins fused with the SUMO protein or ubiquitin.

The purity of preparations was assessed using Sorbfil 1.0 Video Densitometer software, and to this end, the gels stained after electrophoresis were scanned, the resulting image was computerized and the amount of protein in a stain and each track was assessed using the above software. As the standards for comparison, highly purified preparations of the analyzed proteins were used, the known amount of which was applied on the adjacent tracks in the same gel. The purity of protein preparations assessed by such method was 96% and higher.

Example 10

Production of 1F9 and 2E12 Proteins by the Saccharomyces cerevisiae VKPM Y-3583 and VKPM Y-3584 Strains In order to obtain the inoculum, VKPM Y-3583 and VKPM Y-3584 strain were grown in the YPD medium on a rotary shaker operating at 250 rpm and 28° C. for 20-24 hours. 50 ml of the inoculum was used for inoculation of 3-liter Anglicon fermentor containing 950 ml of the YPD medium. Fermentation was conducted at 28° C., aeration speed of 1 l/min and mixing rate of 1000 rpm. 24 hours after inoculation of the fermentor, the culture medium was fed with a 50% glucose solution at a rate of 2 ml/hr and pH-stating of the culture was established at pH 6.8±0.1 using the solutions of 10% sulphuric acid and 10% NaOH for subtitration. The average total fermentation time was 72 hours. According to the electrophoretic analysis, the production of 1F9 under these conditions was at least 200 mg/l of the culture liquid and the production of 2E12 under these conditions was at least 100 mg/l of the culture liquid.

Example 11

Isolation and Purification of the Recombinant 1F9 and 2E12 Proteins from the Water Insoluble Fractions of Saccharomyces cerevisiae Cells 1F9 and 2E12 proteins were isolated and purified from the water insoluble fractions of the VKPM Y-3583 and VKPM Y-3583 producer strain cells using the methods described by Bogush et. al. [Bogush V. G. at al., 2001, Biotechnologies, v. 2, 11-22; Bogush V. G. at al., 2006, Biotechnologies, v. 4, 3-12; Bogush V. G. et al., 2009, J. Neuroimmune Pharmacol., v. 4, 17-27]. The S. cerevisiae yeast biomass was grown in a 3-liter fermentor on the YPD medium without feeding in the presence of 2% glucose in the starting medium to yield at an average 400-500 g of the humid cell biomass from a single fermentation. 1 kg of the washed humid biomass was suspended in a "breakdown buffer" for breaking down the cells using the glass beads in a flow mill for 1.5 hour, the resulting suspension was centrifuged and the precipitate was collected. The target protein was extracted from the precipitate using a solution of 10% lithium chloride in 90% formic acid for 16-18 hours followed by centrifugation. The precipitate was discarded, and the supernatant was subjected to ultrafiltration followed by diafiltration through a M50 membrane to render 10 mM sodium acetate, pH 4.0 and remove the host cell proteins with a molecular weight lower than 50 kDa.

Final purification was accomplished using ion-exchange chromatography on a HiPrep 16/10 SP FF cation-exchange column (GE Healthcare) in the FPLS system. After passing the filtrate through the column and washing the column with a 10 mM sodium phosphate buffer, pH 7.0 and then with a 10 mM sodium acetate buffer, pH 4.0, 1F9 and 2E12 proteins were eluted from the column with a 10% NaCl solution in the same buffer and electrophoretically identified in a 12% PAAS-DDS-Na, the fractions with the target protein were combined, dialyzed against the deionized water, frozen at −7° C. and lyophilized. The lyophilized preparation comprises a white color substance similar to the cotton.

Example 12

Characterization of the 1F9 and 2E12 Proteins

In order to analyze the obtained preparation of the pure recombinant protein, a batch of the preparation was preliminary dissolved in 90% formic acid with 10% lithium chloride for at least 2 hours, dialyzed against the deionized water (for 1-1.5 hour) and analyzed using the SDS-electrophoresis in 12% PAAG. The presence of one band in the gel corresponding to the molecular weight of the recombinant protein was is indicative of homogeneity of the resulting preparation. The obtained preparations of both proteins were characterized by an extinction coefficient of approximately 0.48±0.02 $RU_{280}$/mg. This value agreed with the theoretical value calculated based on the amino acid composition of these proteins (0.49 $RU_{280}$/M) and was indicative of a high purity of the obtained preparations.

In order to analyze the ability of the purified recombinant proteins of the orb weaving spider silk to form various types of supramolecular structures, these proteins were tested for the ability to form water insoluble threads. The threads were obtained by spinning a concentrated protein solution through a narrow orifice. To this end, a batch of the purified and lyophilized protein preparation was dissolved in 90% formic acid with 10%—lithium chloride for at least 2 hours, dialyzed against the deionized water for 1-1.5 hour, and the undissolved material was removed by centrifugation. The protein solution was passed through a custom-built microspinneret with an internal diameter of about 50 μm at a rate of 5-10 μl/min into a coagulation bath with 96% ethanol. As a result, a water insoluble thread was formed freely falling to the vessel bottom. The newly formed artificial threads in the ethanol vessel are shown in FIG. 8. The newly formed artificial threads were kept in a vessel with 96% alcohol for 20 minutes and then extended as much as possible in 75% ethanol, annealed, kept in the deionized water and air dried. The threads exposed to all stages were characterized by the values of the relative breaking load of 10-15 cN/tex (13 MPa).

The above results show that the proposed method for producing the recombinant proteins of the orb weaving spider silk enables a significant increase in the yield of the recombinant proteins, wherein the resulting recombinant proteins are characterized by a high purity and physico-chemical properties typical for the natural spider silk proteins. The proposed method for producing the spider silk recombinant protein makes it possible to produce very high-purity recombinant protein preparations on an industrial scale, to develop the microspinning methods for producing artificial fibers on the basis thereof, as well as the methods for forming films, hydrogels, microgels and microcapsules on the basis of the spider silk recombinant proteins for use in biotechnologies, medicine, cosmetology, automobile and aircraft industry and other fields.

The invention claimed is:

1. A method for producing a recombinant orb weaving spider silk protein in the yeast cells, comprising constructing an expression vector comprising a DNA sequence encoding the recombinant orb weaving spider silk protein, transforming the yeast cells with the expression vector, and expressing the recombinant orb weaving spider silk protein in the transformed yeast cells, wherein the expression vector is pPDX3-HUB-2E12 bireplicon vector including a replication initiation region of the endogenic 2-μm yeast plasmid, a GAL1 gene yeast promotor region, a DNA sequence encoding the recombinant 2E12 protein of the *Nephila madagascariensis* orb weaving spider dragline silk and fused with a DNA sequence encoding *Saccharomyces cerevisiae* ubiquitin.

2. A method for producing a recombinant orb weaving spider silk protein in the yeast cells, comprising constructing an expression vector comprising a DNA sequence encoding the recombinant orb weaving spider silk protein, transforming the yeast cells with the expression vector, and expressing the recombinant orb weaving spider silk protein in the transformed yeast cells, wherein the expression vector is pPDX3-HUB-1F9 bireplicon vector including a replication initiation region of the endogenic 2-μm yeast plasmid, a GAL1 gene yeast promotor region, a DNA sequence encoding the recombinant 1F9 protein of the *Nephila clavipes* orb weaving spider dragline silk and fused with a DNA sequence encoding *Saccharomyces cerevisiae* ubiquitin.

3. A method for producing a recombinant orb weaving spider silk protein in the yeast cells, comprising constructing an expression vector comprising a DNA sequence encoding the recombinant orb weaving spider silk protein, transforming the yeast cells with the expression vector, and expressing the recombinant orb weaving spider silk protein in the transformed yeast cells, wherein the expression vector is pPDX3-SUMO-1F9 bireplicon vector including a replication initiation region of the endogenic 2-μm yeast plasmid, a GAL1 gene yeast promotor region, a DNA sequence encoding the recombinant 1F9 protein of the *Nephila clavipes* orb weaving spider dragline silk and fused with a DNA sequence encoding *Saccharomyces cerevisiae* SUMO protein.

* * * * *